US007829663B2

(12) United States Patent
Kornecki et al.

(10) Patent No.: US 7,829,663 B2
(45) Date of Patent: Nov. 9, 2010

(54) F11 RECEPTOR (F11R) ANTAGONISTS AS THERAPEUTIC AGENTS

(76) Inventors: Elizabeth Kornecki, 7 Bayview Pl., Staten Island, NY (US) 10304; Anna Babinska, 9 Vogel La., Staten Island, NY (US) 10314; Yigal H. Ehrlich, 7 Bayview Pl., Staten Island, NY (US) 10304

(*) Notice: Subject to any disclaimer, the term of this patent is extended or adjusted under 35 U.S.C. 154(b) by 0 days.

(21) Appl. No.: 12/141,635

(22) Filed: Jun. 18, 2008

(65) Prior Publication Data
US 2009/0170779 A1 Jul. 2, 2009

Related U.S. Application Data

(60) Division of application No. 11/173,037, filed on Jul. 1, 2005, now abandoned, which is a continuation-in-part of application No. PCT/US2003/039890, filed on Dec. 16, 2003.

(60) Provisional application No. 60/438,669, filed on Jan. 3, 2003.

(51) Int. Cl.
*A61K 38/00* (2006.01)
*A61K 38/16* (2006.01)
*A61K 38/10* (2006.01)
*A61K 39/00* (2006.01)

(52) U.S. Cl. ............ 530/300; 530/326; 530/327; 514/13; 514/14; 424/185.1; 424/198.1

(58) Field of Classification Search ............ None
See application file for complete search history.

(56) References Cited

U.S. PATENT DOCUMENTS

| 4,946,778 | A | 8/1990 | Ladner et al. |
| 5,051,448 | A | 9/1991 | Shashoua |
| 5,169,862 | A | 12/1992 | Burke, Jr. et al. |
| 5,192,746 | A | 3/1993 | Lobl et al. |
| 5,359,046 | A | 10/1994 | Capon et al. |
| 5,539,085 | A | 7/1996 | Bischoff et al. |
| 5,559,103 | A | 9/1996 | Gaeta et al. |
| 5,576,423 | A | 11/1996 | Aversa et al. |
| 5,665,701 | A | 9/1997 | Kornecki et al. |
| 6,150,502 | A | 11/2000 | Strachan |
| 6,358,707 | B1 | 3/2002 | Gupta et al. |
| 6,699,688 | B1 | 3/2004 | Kornecki et al. |
| 2004/0115135 | A1* | 6/2004 | Quay ............ 424/46 |

FOREIGN PATENT DOCUMENTS

| EP | 0 045 665 | 2/1982 |
| EP | 0 125 023 | 11/1984 |
| EP | 0 171 496 | 2/1986 |
| EP | 0 173 494 | 3/1986 |
| EP | 0 184 187 | 6/1986 |
| WO | WO 86/01533 | 3/1986 |
| WO | WO 87/02671 | 5/1987 |
| WO | WO 99/02561 | 1/1999 |
| WO | WO 2004/063327 | 7/2004 |

OTHER PUBLICATIONS

Karsan A. et al., "The Blood Vessel Wall", In Hematology: Basic Principles and Practice, 3rd Ed. 1770-1782 (2000).
Cines D.B. et al., "Endothelial Cells in Physiology and in the Pathophysiology of Vascular Disorders", Blood 91(10):3527-3561 (1998).
May A.E. et al., "The Relevance of Blood Cell-Vessel Wall Adhesive Interactions for Vascular Thrombotic Disease", Thrombosis and Haemostasis 82(2):962-970 (1999).
Diquélou A. et al., "Relationship Between Endothelial Tissue Factor and Thrombogenesis Under Blood Flow Conditions", Thrombosis and Haemostasis 74(2):778-783 (1995).
Dardik R. et al., "Recombinant Fragment of Von Willebrand Factor AR545C Inhibits Platelet Binding to Thrombin and Platelet Adhesion to Thrombin-Treated Endothelial Cells", British Journal of Haematology 109:512-518 (2000).
André P. et al., "Platelets Adhere to and Translocate on Von Willebrand Factor Presented by Endothelium in Stimulated Veins", Blood 96(10):3322-3328 (2000).
Rosenblum W.I. et al., "Role of Platelet-Endothelial Cell Adhesion Molecule (PECAM) in Platelet Adhesion/Aggregation Over Injured but Not Denuded Endothelium In Vivo and Ex Vivo", Stroke 27(4):709-711 (1996).
Bombeli T. et al., "Adhesion of Activated Platelets to Endothelial Cells: Evidence for a GPIIbIIa-Dependent Bridging Mechanism and Novel Roles for Endothelial Intercellular Adhesion Molecule 1 (ICAM-1), $\alpha_v\beta_3$ Integrin, and GPIb$\alpha$", J. Exp. Med. 187(3):329-339 (1998).
Verheul H.M.W. et al., "Vascular Endothelial Growth Factor-Stimulated Endothelial Cells Promote Adhesion and Activation of Platelets", Blood 96(13):4216-4221 (2000).
Kornecki E. et al., "Activation of Human Platelets by a Stimulatory Monoclonal Antibody", The Journal of Biological Chemistry 265(17):10042-10048 (1990).
Naik U.P. et al., "Mechanisms of Platelet Activation by a Stimulatory Antibody: Cross-Linking of a Novel Platelet Receptor for Monoclonal Antibody F11 with the Fc$\gamma$RII Receptor", Biochem. J. 310:155-162 (1995).

(Continued)

*Primary Examiner*—Robert Landsman
*Assistant Examiner*—Bruce D Hissong
(74) *Attorney, Agent, or Firm*—Scully, Scott, Murphy & Presser, P.C.

(57) ABSTRACT

The present invention provides a cell adhesion molecule (CAM), designated F11 receptor (F11R), which is a member of the immunoglobulin super family localized on the surface of human platelets, and determined to effect platelet aggregation, secretion, platelet spreading and cellular adhesion. Cloned F11R cDNA and full length F11R cDNA and amino acid sequences are provided. F11R-antagonists and methods for the prevention and treatment of thrombosis, atherosclerosis, heart attacks, stroke and other clinical disorders involving thrombus formation are also provided.

4 Claims, 10 Drawing Sheets

OTHER PUBLICATIONS

Martin-Padura I. et al., "Junctional Adhesion Molecule, a Novel Member of the Immunoglobulin Superfamily that Distributes at Intercellular Junctions and Modulates Monocyte Transmigration", *The Journal of Cell Biology* 142(1):117-127 (1998).

Kornecki E. et al., "Identification of a Unique Type of Thrombopathy of Human Platelets: Defect in the Exposure of Active Fibrinogen Receptors in a Patient with Friedreich's Ataxia", *J. Lab Clin. Med.* 111:618-626 (1988).

Wang F. et al., "Stimulatory Antibody-Induced Activation and Selective Translocation of Protein Kinase C Isoenzymes in Human Platelets", *Biochem. J.* 311:401-406 (1995).

Sobocka M. et al., "Molecular Mechanisms of Platelet Activation by a Stimulatory Monoclonal Antibody, Cloning and Potential Pathophysiological Roles for a Novel Platelet Receptor", *Blood* 90(10), *Supplement* 1 (part 2 of 2):2996 (1997).

Sobocka M.B. et al., "Cloning of the Human Platelet F11 Receptor: A Cell Adhesion Molecule Member of the Immunoglobulin Superfamily Involved in Platelet Aggregation", *Blood* 95(8):2600-2609 (2000).

Babinska A. et al., "Two Regions of the Human Platelet F11-Receptor (F11R) Are Critical for Platelet Aggregation, Potentiation and Adhesion", *Thromb Haemost* 87:712-721 (2002).

Ozaki H. et al., "Cutting Edge: Combined Treatment of TNF-α and IFN-γ Causes Redistribution of Junctional Adhesion Molecule in Human Endothelial Cells", *The Journal of Immunology* 163:553-557 (1999).

Williams L.A. et al., "Identification and Characterisation of Human Junctional Adhesion Molecule (JAM)", *Molecular Immunology* 36:1175-1188 (1999).

Liu Y. et al., "Human Junction Adhesion Molecule Regulates Tight Junction Resealing in Epithelia", *Journal of Cell Science* 113:2363-2374 (2000).

Gupta S.K. et al., "Platelet Agonist F11 Receptor Is a Member of the Immunoglobulin Superfamily and Identical with Junctional Adhesion Molecule (JAM): Regulation of Expression in Human Endothelial Cells and Macrophages", *IUBMB Life* 50:51-56 (2000).

Naik U.P. et al., "Characterization and Chromosomal Localization of JAM-1, a Platelet Receptor for a Stimulatory Monoclonal Antibody", *Journal of Cell Science* 114(3):539-547 (2000).

Sobocka M.B. et al., "F11 Receptor-Mediated Potentiation of Platelet Activation by Subthreshold Concentrations of Physiological Agonists", *XVIII Congress*, Abstract #P1902 (2001).

Babine R.E. et al., "Molecular Recognition of Protein-Ligand Complexes: Applications to Drug Design", *Chem. Rev.* 97:1359-1472 (1997).

Hanessian S. et al., "Design and Synthesis of Conformationally Constrained Amino Acids as Versatile Scaffolds and Peptide Mimetics", *Tetrahedron* 53(37-39):12789-12854 (1997).

Fletcher M.D. et al., "Partially Modified Retro-Inverso Peptides: Development, Synthesis, and Conformational Behavior", *Chemical Reviews* 98(2):763-795 (1998).

Morley J.S., "Modulation of the Action of Regulatory Peptides by Structural Modification", *Trends Pharm. Sci.*, 463-468 (1980).

Hudson D. et al., "Methionine Enkephalin and Isosteric Analogues", *Int. J. Peptide Protein Res.* 14:177-185 (1979).

Spatola A.F. et al., "Structure-Activity Relationships of Enkephalins Containing Serially Replaced Thiomethylene Amide Bond Surrogates", *Life Sciences* 38(14):1243-1249 (1986).

Hann M.M. et al., "On the Double Bond Isostere of the Peptide Bond: Preparation of an Enkephalin Analogue", *J. Chem. Soc. Perkin Trans. I*, 307-314 (1982).

Almquist R.G. et al., "Synthesis and Biological Activity of a Ketomethylene Analogue of a Tripeptide Inhibitor of Angiotensin Converting Enzyme", *Journal of Medicinal Chemistry* 23(12):1392-1398 (1980).

Jennings-White C. et al., "Synthesis of Ketomethylene Analogs of Dipeptides", *Tetrahedron Letters* 23(25):2533-2534 (1982).

Holladay M.W. et al., "Synthesis of Hydroxyethylene and Ketomethylene Dipeptide Isosteres", *Tetrahedron Letters* 24(41):4401-4404 (1983).

Hruby V.J., "Conformational Restrictions of Biologically Active Peptides Via Amino Acid Side Chain Groups", *Life Sciences* 31(3):189-199 (1982).

Eldred C.D. et al., "Orally Active Non-Peptide Fibrinogen Receptor (GpIIb/IIIa) Antagonists: Identification of 4-[4-[4-(Aminoiminomethyl)phenyl]-1-piperazinyl]-1-piperidineacetic Acid as a Long-Acting, Broad-Spectrum Antithrombotic Agent", *Journal of Medicinal Chemistry* 37(23):3882-3885 (1994).

Ku T.W. et al., "Potent Non-Peptide Fibrinogen Receptor Antagonists Which Present an Alternative Pharmacophore", *Journal of Medicinal Chemistry* 38(1):9-12 (1995).

Ferguson M.A.J. et al., "Cell-Surface Anchoring of Proteins Via Glycosyl-Phosphatidylinositol Structures", *Ann. Rev. Biochem.* 57:285-320 (1988).

Noren C.J. et al., "A General Method for Site-Specific Incorporation of Unnatural Amino Acids into Proteins", *Science* 244:182-188 (1989).

Farmer P.S., "Bridging the Gap Between Bioactive Peptides and Nonpeptides: Some Perspectives in Design", *Drug Design* (E.J. Ariëns, ed.) 10:119-143 (1980).

Ball J.B. et al., "Conformational Constraints: Nonpeptide β—Turn Mimics", *Journal of Molecular Recognition* 3(2):55-64 (1990).

Freidinger R.M., "Non-Peptide Ligands for Peptide Receptors", *Trends Pharmacol. Sci.* 10:270-274 (1989).

Merrifield R.B., "Solid Phase Peptide Synthesis. I. The Synthesis of a Tetrapeptide", *J. Am. Chem. Soc.* 85:2149-2154 (1963).

Matteucci M.D. et al., "Synthesis of Deoxyoligonucleotides on a Polymer Support", *J. Am. Chem. Soc.* 103(11):3185-3191 (1981).

Bedzyk W.D. et al., "Immunological and Structural Characterization of a High Affinity Anti-Fluorescein Single-Chain Antibody", *The Journal of Biological Chemistry* 265(30):18615-18620 (1990).

Chaudhary V.K. et al., "A Recombinant Single-Chain Immunotoxin Composed of Anti-Tac Variable Regions and a Truncated Diphtheria Toxin", *Proc. Natl. Acad. Sci. USA* 87:9491-9494 (1990).

Kohler et al., "Continuous Cultures of Fused Cells Secreting Antibody of Predefined Specificity", *Nature* 256:495-497 (1975).

Liu A.Y. et al., "Chimeric Mouse-Human IgG1 Antibody that Can Mediate Lysis of Cancer Cells", *Proc. Natl. Acad. Sci. USA* 84:3439-3443 (1987).

Sun L.K. et al., "Chimeric Antibody with Human Constant Regions and Mouse Variable Regions Directed Against Carcinoma-Associated Antigen 17-1A", *Proc. Natl. Acad. Sci. USA* 84:214-218 (1987).

Better M. et al., "*Escherichia coli* Secretion of an Active Chimeric Antibody Fragment", *Science* 240:1041-1043 (1988).

Tuszynski G.P. et al., "Spectrophotometric Quantitation of Anchorage-Dependent Cell Numbers Using the Bicinchoninic Acid Protein Assay Reagent", *Analytical Biochemistry* 184:189-191 (1990).

Kostrewa D. et al., "X-Ray Structure of Junctional Adhesion Molecule: Structural Basis for Hemophilic Adhesion Via a Novel Dimerization Motif", *The EMBO Journal* 20(16):4391-4398 (2001).

* cited by examiner

FIGURE 6

F11R cDNA sequence (full length)

agtggcctgatcgcgatggggacaaaggcgcaagtcgagaggaaactgttgtgcctcttcatattggcgatcctgttgtgctccct ggcattgggcagtgttacagtgcactcttctgaacctgaagtcagaattcctgagaataatcctgtgaagttgtcctgtgcctactcg ggcttttcttctccccgtgtggagtggaagtttgaccaaggagacaccaccagactcgtttgctataataacaagatcacagcttcct atgaggaccgggtgaccttcttgccaactggtatcaccttcaagtccgtgacacgggaagacactgggacatacacttgtatggtc tctgaggaaggcggcaacagctatggggaggtcaaggtcaagctcatcgtgcttgtgcctccatccaagcctacagttaacatcc cctcctctgccaccattgggaaccgggcagtgctgacatgctcagaacaagatggttccccaccttctgaatacacctggttcaaa gatgggatagtgatgcctacgaatcccaaaagcacccgtgccttcagcaactcttcctatgtcctgaatcccacaacaggagagct ggtctttgatcccctgtcagcctctgatactggagaatacagctgtgaggcacggaatgggtatgggacacccatgacttcaaatg ctgtgcgcatggaagctgtggagcggaatgtgggggtcatcgtggcagccgtccttgtaaccctgattctcctgggaatcttggttt ttggcatctggtttgcctatagccgaggccactttgacagaacaaagaaagggacttcgagtaagaaggtgatttacagccagcct agtgcccgaagtgaaggagaattcaaacagacctcgtcattcctggtgtgagcctggtcggctcaccgcctatcatctgcatttgc cttactcaggtgctaccggactctggccctgatgtctgtagtttcacaggatgccttatttgtcttctacaccccacagggcccccta cttcttcggatgtgttttaataatgtcagctatgtgccccatcctccttcatgccctccctcccttcctaccactgctgagtggcctgg aacttgtttaaagtgtttattcctcatttctttgagggatcaggaaggaatcctgggtatgccattgacttcccttctaagtagacagca aaaatggcgggggtcgcaggaatctgcactcaactgcccacctggctggcagggatctttgaataggtatcttgagcttggttctg ggctctttccttgtgtactgacgaccagggccagctgttctagagcgggaattagaggctagagcggctgaaatggttgtttggtg atgacactggggtccttccatctctggggcccactctcttctgtcttcccatgggaagtgccactgggatccctctgccctgtcctcc tgaatacaagctgactgacattgactgtgtctgtggaaa FIGURE 6 (continued)

atgggagctcttgttgtggagagcatagtaaattttcagagaacttgaagccaaaaggatttaaaaccgctgctctaaagaaaaga aaactggaggctgggcgcagtggctcacgcctataatcccagaggctgaggcaggcggatcacctgaggtcaggagtt caggatcagcctgaccaacatggagaaaccctgctggaaatacaaagttagccaggcatggtggtgcatgcctgtagtcccagc tgctcaggagcctggcaacaagagcaaaactccagctcaaaaaaaaaaaaaaaaa

FIGURE 7

F11R amino acid sequence mgtkaqverkllclfilaillcslalgsvtvhssepevripennpvklscaysgfssprvewkfdqgdttrlvcynnkitasyedr vtflptgitfksvtredtgtytcmvseeggnsygevkvklivlvppskptvnipssatignravltcseqdgsppseytwfkdgi vmptnpkstrafsnssyvlnpttgelvfdplsasdtgeyscearngygtpmtsnavrmeavernvgvivaavlvtlillgilvf giwfaysrghfdrtkkgtsskkviysqpsarsegefkqtssflv

SEQUENCE LISTING

```
<160> NUMBER OF SEQ ID NOS: 9

<210> SEQ ID NO 1
<211> LENGTH: 23
<212> TYPE: PRT
<213> ORGANISM: Homo sapiens

<400> SEQUENCE: 1

Ser Val Thr Val His Ser Ser Glu Pro Glu Val Arg Ile Pro Glu Asn
1               5                   10                  15

Asn Pro Val Lys Leu Ser Cys
            20

<210> SEQ ID NO 2
<211> LENGTH: 22
<212> TYPE: PRT
<213> ORGANISM: Homo sapiens

<400> SEQUENCE: 2

Ser Tyr Glu Asp Arg Val Thr Phe Leu Pro Thr Gly Ile Thr Phe Lys
1               5                   10                  15

Ser Val Thr Arg Glu Asp
            20
```

<210> SEQ ID NO 3
<211> LENGTH: 22
<212> TYPE: PRT
<213> ORGANISM: Homo sapiens

<400> SEQUENCE: 3

Trp Lys Phe Asp Gln Gly Asp Thr Thr Arg Leu Val Glu Tyr Asn Asn
1               5                   10                  15

Lys Ile Thr Ala Ser Tyr
            20

<210> SEQ ID NO 4
<211> LENGTH: 13
<212> TYPE: PRT
<213> ORGANISM: Homo sapiens

<400> SEQUENCE: 4

Lys Ser Val Thr Arg Glu Asp Thr Gly Thr Tyr Thr Cys
1               5                   10

<210> SEQ ID NO 5
<211> LENGTH: 15
<212> TYPE: PRT
<213> ORGANISM: Homo sapiens

<400> SEQUENCE: 5

Glu Gln Asp Gly Ser Pro Pro Ser Glu Tyr Thr Trp Phe Lys Asp
1               5                   10                  15

<210> SEQ ID NO 6
<211> LENGTH: 1816
<212> TYPE: DNA
<213> ORGANISM: Homo sapiens

<400> SEQUENCE: 6

```
agtggcctga tcgcgatggg gacaaaggcg caagtcgaga ggaaactgtt gtgcctcttc      60
atattggcga tcctgttgtg ctccctggca gggcagtgtt acagtgcact cttctgaacc     120
tgaagtcaga attcctgaga ataatcctgt gaagttgtcc tgtgcctact cgggcttttc     180
ttctccccgt gtggagtgga gtttgaccag gagacacc accagactcg tttgctataa       240
taacaagatc acagcttcct atgaggaccg ggtgaccttc ttgccaactg gtatcacctt     300
caagtccgtg acacgggaag acactgggac atacacatgg tctctgagga aggcggcaac    360
agctatgggg aggtcaaggt caagctcatc gtgcttgtgc ctccatccaa gcctacagtt    420
aacatcccct cctctgccac cattgggaac cgggcagtgc tgacatgctc agaacaagat    480
ggttccccac cttctgaata cacctggttc aaagatggga tagtgatgcc tacgaatccc    540
aaaagcaccc gtgccttcag caactcttcc tatgtcctga atccacacaa cggagagctg    600
gtctttgatc ccctgtcagc ctctgatact ggagaataca gctgtgaggc acggaatggg    660
tatgggacac ccatgacttc aaatgctgtg cgcatggaag ctgtggagcg aatgtgggg    720
gtcatcgtgg cagccgtcct tgtaaccctg attctcctgg aatcttggt ttttggcatc    780
tggtttgcct atagccgagg ccactttgac agaacaaaga aagggacttc gagtaagaag    840
gtgatttaca gccagcctag tgcccgaagt gaaggagaat caaacagac tcgtcattc     900
ctggtgtgag cctggtcggc tcaccgccta tcatctgcat ttgccttact caggtgctac    960
cggactctgg ccctgatgt ctgtagtttt acaggatgcc ttatttgtct tctacacccc   1020
acagggcccc ctacttcttc ggatgtgttt ttaataatgt cagctatgtg ccccatcctc  1080
```

-continued

```
cttcatgccc tccctcccct tcctaccact gctgagtggc ctggaacttg tttaaagtgt    1140
ttattcctca tttctttgag ggatcaggaa ggaatcctgg gtatgccatt gacttccctt    1200
ctaagtagac agcaaaaatg gcggggtcg caggaatctg cactcaactg cccacctggc    1260
tggcagggat cttttgaatag gtatcttgag cttggttctg ggctctttcc ttgtgtactg    1320
acgaccaggg ccagctgttc tagagcggga attagaggct agagcggctg aaatggttgt    1380
ttggtgatga cactggggtc cttccatctc tggggcccac tctcttctgt cttcccatgg    1440
gaagtgccac tgggatccct ctgccctgtc ctcctgaata caagctgact gacattgact    1500
gtgtctgtgg aaaatgggag ctcttgttgt ggagagcata gtaaattttc agagaacttg    1560
aagccaaaag gatttaaaac cgctgctcta agaaaagaa aactggaggc tgggcgcagt    1620
ggctcacgcc tataatccca gaggctgagg caggcggatc acctgaggtc aggagttcag    1680
gatcagcctg accaacatgg agaaaccctg ctggaaatac aaagttagcc aggcatggtg    1740
gtgcatgcct gtagtcccag ctgctcagga gcctggcaac aagagcaaaa ctccagctca    1800
aaaaaaaaaa aaaaaa    1816
```

<210> SEQ ID NO 7
<211> LENGTH: 299
<212> TYPE: PRT
<213> ORGANISM: Homo sapiens

<400> SEQUENCE: 7

```
Met Gly Thr Lys Ala Gln Val Glu Arg Lys Leu Leu Cys Leu Phe Ile
1               5                  10                  15

Leu Ala Ile Leu Leu Cys Ser Leu Ala Leu Gly Ser Val Thr Val His
            20                  25                  30

Ser Ser Glu Pro Glu Val Arg Ile Pro Glu Asn Asn Pro Val Lys Leu
        35                  40                  45

Ser Cys Ala Tyr Ser Gly Phe Ser Ser Pro Arg Val Glu Trp Lys Phe
    50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
        195                 200                 205

Glu Tyr Ser Cys Glu Ala Arg Asn Gly Tyr Gly Thr Pro Met Thr Ser
    210                 215                 220

Asn Ala Val Arg Met Glu Ala Val Glu Arg Asn Val Gly Val Ile Val
225                 230                 235                 240
```

-continued

```
Ala Ala Val Leu Val Thr Leu Ile Leu Leu Gly Ile Leu Val Phe Gly
            245                 250                 255
Ile Trp Phe Ala Tyr Ser Arg Gly His Phe Asp Arg Thr Lys Lys Gly
            260                 265                 270
Thr Ser Ser Lys Lys Val Ile Tyr Ser Gln Pro Ser Ala Arg Ser Glu
            275                 280                 285
Gly Glu Phe Lys Gln Thr Ser Ser Phe Leu Val
        290                 295

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide sequence. A forward
      primer to human F11 receptor cDNA.

<400> SEQUENCE: 8
gcgggatcca tcgcgatggg gacaaaggcg                                    30

<210> SEQ ID NO 9
<211> LENGTH: 36
<212> TYPE: DNA
<213> ORGANISM: Artificial Sequence
<220> FEATURE:
<223> OTHER INFORMATION: synthetic oligonucleotide sequence. A reverse
      primer to human F11 receptor cDNA.

<400> SEQUENCE: 9
ccgacctcga gcggcattcc gctccacagc ttccat                             36
```

F11 RECEPTOR (F11R) ANTAGONISTS AS THERAPEUTIC AGENTS

CROSS REFERENCE TO RELATED APPLICATIONS

This application is a divisional of application Ser. No. 11/173,037, filed Jul. 1, 2005 now abandoned, which is a continuation-in-part of the national phase of PCT/US2003/039890 having an international filing date of Dec. 16, 2003, which claims priority from U.S. Provisional Application No. 60/438,669, filed on Jan. 3, 2003.

FIELD OF THE INVENTION

The present invention relates to protein and peptide chemistry, as well as crystallography and organic chemistry. The present invention is directed to a cell adhesion molecule (CAM) and fragments thereof and more particularly to a CAM designated as the F11 receptor (F11R), or a polypeptide fragment thereof. The present invention also relates to F11R-antagonists and methods for the prevention and treatment of excessive bleeding following a wound injury, inflammatory diseases of the nervous system, thrombosis, inflammatory thrombosis, atherothrombosis, angiogenesis, plaque formation, cancer, immunothrombocytopenia (ITP), heart attacks, stroke, disorders of platelet and endothelial cell dysfunctions and other disorders involving thrombus formation.

BACKGROUND OF THE INVENTION

The vasculature is recognized as a dynamic metabolic organ that exists under normal physiological conditions in an intact, undisturbed state (Karsan, et al. *In: Hematology: Basic Principles and Practice,* 3rd Ed. Hoffman, et al. (eds) 2000; pp. 1770-82). Endothelial cells (EC), which line the exposed (luminal) surface of blood vessels, are normally not thrombogenic. That is, healthy EC do not attract nor bind circulating platelets (Cines, et al. Blood 1998, 91: 3527-61; May, et al. *Thromb Haemost* 1999, 82: 962-70). It is well known that the physiological function of the endothelium is to facilitate blood flow by providing a highly thromboresistant surface to flowing blood that inhibits platelet adhesion and clotting (Cines, et al.). However, under inflammatory conditions, the nonthrombotic surface of EC can be transformed to a prothrombotic surface following exposure to cytokines (May, et al.; Diquelou et al. *Thromb Haemost* 1995, 74: 778-83), resulting in procoagulant activity and a predisposition to thrombosis (May, et al.; Dardik, et al. *Br J Haemarol.* 2000, 109:512-8; Andre, et al. *Blood* 2000, 96:3322-8). Indeed, the adhesion, accumulation and recruitment of non-stimulated platelets on cytokine-stimulated EC have been reported, with studies implicating the Platelet Endothelial Cell Adhesion Molecule-1 (PECAM-1; Rosenblum, et al. *Stroke* 1995, 27:709-11); beta 1 integrin (Bombeli et al. *J Exp. Med* 1998, 187:329-39), von Willebrand factor (Dardik, et al.; Andre, et al.), and tissue factor (Verheul, et al. *Blood* 2000, 96:4216-21) in these processes. Thus, under inflammatory conditions, cytokines induce alterations in EC which result in the adhesion of non-stimulated platelets.

Recently, a novel adhesion protein of the immunoglobulin (Ig) superfamily has been described with properties indicating a potential triggering role in the pathogenesis of inflammatory thrombosis, atherosclerosis and other disorders involving thrombosis formation. This protein was identified first on the surface of human platelets and called the F11 receptor (F11R; Kornecki, et al. *J Biol Chem* 1990, 265: 10042-8; Naik, et al. *Biochem J* 1995, 311: 155-62), and then on the surface of murine endothelial and epithelial cells and called JAM (Martin-Padura, et al. *J. Cell Biol.* 1998, 142:117-27.).

The human platelet F11 receptor (F11R) is a surface glycoprotein duplex (32 and 35 kD at core protein: 29 kDa) member of the immunoglobulin superfamily. The F11R was first discovered as the target of a potent stimulatory monoclonal antibody, M.Ab.F11, that induces platelet secretion followed by aggregation (Kornecki, et al.; Naik, et al.; Kornecki, et al. *J Lab Clin. Med.* 1988, 111:618-26; Wang et al. *Biochem J.* 1995, 311: 401-6; Kornecki, et al. In: Leukocyte Typing V. Schlossman, et al. (eds.) Oxford University Press 1195: 1241-3; Sobocka, et al. *Blood* 1997, 90: 10, Supplement 1, Part 2, Nov. 15, 2996a.; Sobocka, *Ph.D. Thesis,* 1998: SUNY Downstate, Brooklyn, N.Y., Presented Jun. 10, 1998; published Sep. 15, 1998; Sobocka, et al. *Blood* 2000, 95:2600-9; Babinska, et al. *Thromb Haemost* 2002, 87: 712-21). Signal transduction mechanisms for platelet secretion and aggregation induced by M.Ab.F11 following its initial binding to F11R include: crosslinking of the F11R to the FcγRII (Naik, et al.), activation and translocation of specific PKC isozymes (Wang, et al.), phosphorylation of the F11R through activation of PKC (Naik, et al.; Wang, et al.), phosphorylation of the F11R following induction of platelet aggregation by the physiological agonists thrombin and collagen and by M.Ab.F11 itself (Sobocka, et al. 1997; Sobocka; Sobocka, et al. 2000; Babinska, et al.), and phosphorylation of myosin light chain and pleckstrin, leading to shape change and granular secretion respectively (Kornecki, et al. 1990). Following secretion, this signal transduction pathway culminates in the activation of latent fibrinogen receptors and platelet aggregation (Kornecki, et al. 1990). Partial amino acid sequences representing 30% of the length of purified F11R have been reported Kornecki in 1995 (Naik, et al.). Cloning of the full-length cDNA for the platelet F11R has revealed that it is a cell adhesion molecule (CAM), a member of the immunoglobin superfamily (Sobocka, et al. 1997; Sobocka; Sobocka, et al. 2000). As a CAM, the F11R participates in mechanisms underlying adhesion of platelets, endothelial cells, and epithelial cells (Martin-Padura, et al.; Sobocka, et al. 2000).

The conclusion that, in addition to its role as a receptor that triggers signal transduction leading to secretion, the F11R also serves as a CAM involved in platelet adhesion was supported by the high degree of sequence similarity found between the human platelet F11R and an adhesion protein called Junctional Adhesion Molecule (JAM), a protein found in murine endothelial cells (Martin-Padura, et al. 1998). Comparison of the murine JAM sequence to the previously-reported sequences of the human platelet F11R (Naik, et al.) revealed over 70% homology of JAM to the N-terminus (23 amino acids) of F11R and to two enzyme-digested products of F11R. In addition, both the human platelet F11R core protein and the murine JAM protein were found to contain a single transmembrane domain and two pairs of cysteine residues in their extracellular domains that allow formation of intermolecular disulfide bridges forming characteristic Ig-like folds. It is now well established that the protein referred to as JAM (Martin-Padura, et al, 1998; Ozaki, et al. *J. Immunol* 1999, 163: 553-7; Williams, et al. *Mol. Immunol.* 1999, 36: 1175-88; Liu, et al. *J. Cell Science* 2000, 113: 2363-74; Gupta, et al. *IUBMB Life* 2000, 50: 51-6; Naik, et al. *J. Cell Science* 2001, 114: 539-47), is the murine ortholog of the human F11R (Kornecki, et al 1990; Naik, et al 1995; Kornecki, et al. 1988; Wang, et al.; Kornecki, et al 1995; Sobocka, et al. 1997; Sobocka; Sobocka, et al. 2000; Babinska, et al.). JAM was localized at intercellular junctions of mouse endothelial and epithelial cells (Martin-Padura, et al.). Similarly, the platelet antibody M.Ab.F11 was found to recognize F11R molecules present at intercellular junctions of cultured human umbilical vein endothelial cells (Sobocka, et al. *XVIII ISTH Congress*, July, 2001, Paris, France, Abs# P1902; Babinska et al., manuscript submitted, 2005). A recent study conducted by the inventors (Babinska, et al. 2002) has determined that two domains of F11R are critical for the induction of platelet aggregation by M.Ab.F11 and the adhesion of platelets to M.Ab.F11. Heretofore, the role of F11R in physiological and pathophysiological processes involving the adhesion of platelets to cytokine-inflamed endothelial cells has remained unknown. The inventors have now determined that the N-terminus of F11R and the first Ig fold of F11R contain protein sequences which are critical for the adhesion of platelets to endothelial cells, and that the recombinant soluble F11R protein and F11R-peptides block approximately 60% of the force of adhesion of platelets to cytokine-treated EC, demonstrating the involvement of the F11R protein in platelet-endothelial cell interactions, which under pathological conditions, result in thrombosis, atherosclerosis and other disorders involving thrombosis formation.

SUMMARY OF THE INVENTION

The present invention provides the full length cDNA sequence of the F11 receptor (F11R) (SEQ ID NO: 6) and the encoded F11R amino acid sequence (SEQ ID NO: 7). The present invention also provides F11R-antagonists including peptide antagonists and peptidomimetic drugs that inhibit the biological action of the F11R protein.

The present invention is directed to methods and compositions for treating F11R-mediated disorders such as thrombosis, atherosclerosis, plaque formation, heart attacks, inflammatory diseases of the nervous system, stroke and all other clinical disorders involving thrombus formation, as detailed above. The invention is also directed to methods for the treatment and prevention of excessive bleeding under physiological procedures, including the prevention of excessive bleeding following wound injury. The present invention provides specific compositions containing at least one F11R-antagonist peptide which inhibits, suppresses or causes the cessation of at least one F11R-mediated biological activity in a mammal, and preferably humans. Another embodiment of the present invention is the preparation of peptidomimetic drugs that have a structure that mimics the active site of F11R and thus inhibit its biological action. An example of the relationship of the structure of such a drug to the structure of the F11R protein is the relationship between the structure of morphine and the protein beta-endorphin.

Nucleic acid molecules coding for any of the above F11R-antagonist proteins, fragments and peptides of the present invention, expression vectors which include any of such nucleic acid molecules, as well as related host cells containing such nucleotide sequences or vectors, are also contemplated by the present invention.

Still another embodiment of the present invention is directed to antibodies raised against the F11R-antagonist proteins, fragments, peptidomimetics and peptides of the present invention.

Preferably, the antibodies of the present invention are raised against those F11R sequences and F11R-antagonist peptides whose sequences coincide with the corresponding sequences of a mammalian F11R or Junctional Adhesion Molecule (JAM) proteins. The antibodies of the present invention can recognize, antagonize or neutralize the activity of F11R. Both polyclonal antibodies and monoclonal antibodies of various chimeric combinations are contemplated by the present invention. Examples of such antibodies include M.Ab.F11.

These and other embodiments of the invention will be readily apparent to those of ordinary skill in view of the disclosure herein.

BRIEF DESCRIPTION OF THE FIGURES

FIG. 2 shows that potentiation of ADP-induced platelet aggregation by M.Ab.F11 is blocked by F11R peptides (SEQ ID NO: 1 and SEQ ID NO: 4).

FIG. 6 provides the F11R cDNA sequence (full length) (SEQ ID NO: 6).

FIG. 7 provides the F11R amino acid sequence (SEQ ID NO: 7).

DETAILED DESCRIPTION OF THE INVENTION

Figure 1:
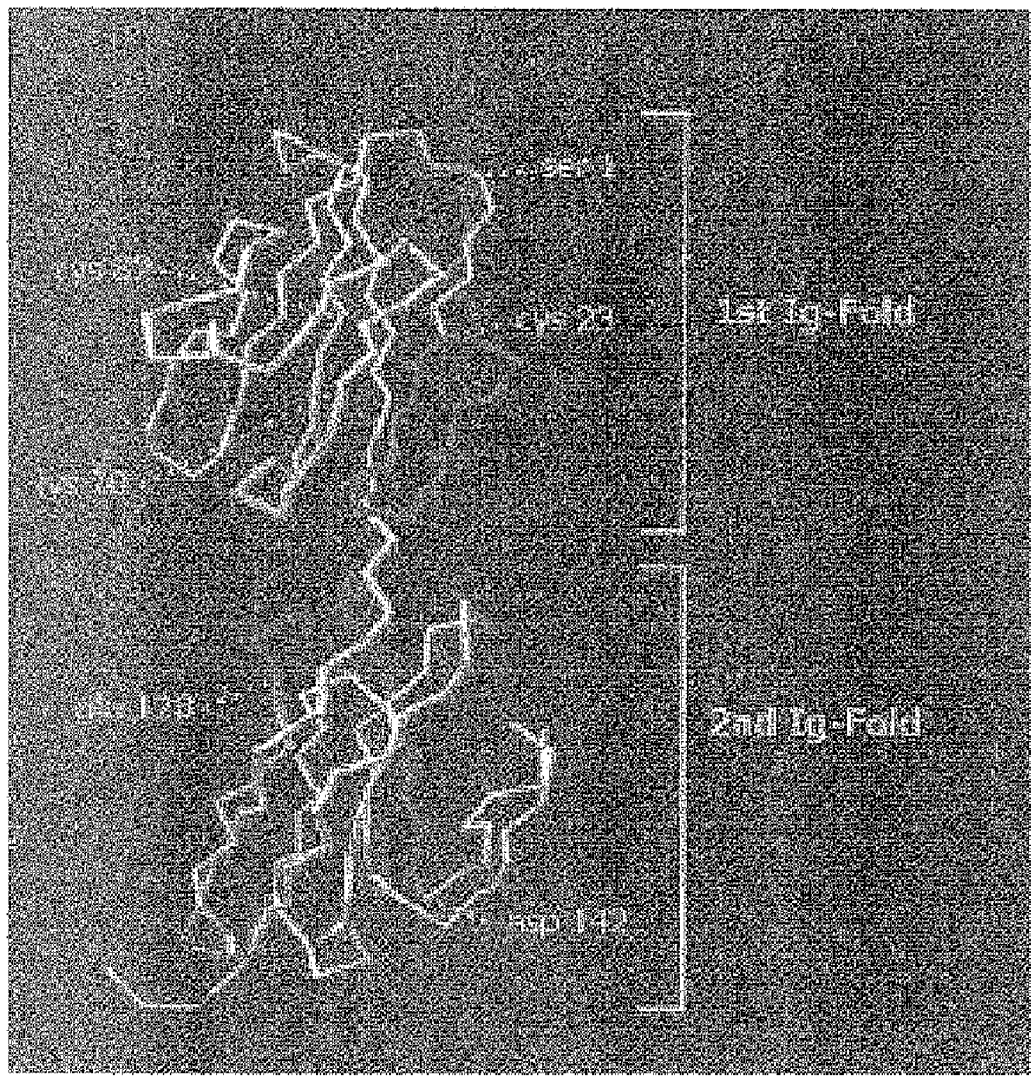
FIG. 1 shows the 3-D structure of the external domain of the mature human platelet F11R. The two Ig-like folds of the human recombinant F11R protein (F11R) are shown as a backbone structure based on the template of the mouse JAM which shares about 70% homology to that of human F11R.

The present invention is directed to F11R-antagonists. By "F11R-antagonist" is meant molecules that inhibit, suppress or cause the cessation of at least one F11R-mediated biological activity by, e.g., interfering with, blocking or otherwise preventing or regulating the interaction or binding of F11R to its target, e.g. F11R on another cell, or another protein that F11R binds to such as itself or other JAMs, to the leukocyte function associated antigen-1 (LFA-1)(Ostermann et al., 2002, Nat. Immunol. 3, 151-158), the integrins GPIIbIIa and alpha,beta3, as well as other binding proteins.

In accordance with the present invention, novel F11R-antagonist peptides derived from or corresponding to the F11R have been isolated and synthesized. These peptides possess F11R antagonistic properties including the ability to selectively bind to F11R and inhibit F11R-mediated biological activity which, for example, is associated with adhesion of platelets to endothelial cells in mammals. The peptides of the present invention preferably correspond to specific portions of the native human F11 receptor and include variations thereof, and therefore are non-immunogenic when administered to humans. The peptides of the present invention can effectively block collagen-induced platelet aggregation and secretion and thereby are efficacious in regard to, inter alia, the prevention of excessive bleeding following an injury, under physiological conditions. Moreover, under pathological conditions, the uncontrolled accumulation of platelets at exposed collagen sites within the injured vasculature results in excessive platelet aggregation, plaque and thrombus formation, atherosclerosis and stroke. The collagen-induced platelet aggregation blocking ability of the F11R-antagonist peptides of the present invention provides heretofore unrecognized treatment and prevention options for diseases and disorders associated with excessive platelet aggregation.

The F11R-antagonist peptides of the present invention substantially correspond to the amino acids of the N-terminus or first Ig domain of human F11R.

A preferred F11R-antagonist peptide of the present invention is a sequence of the N-terminal peptide of the F11R structure:

```
SVTVHSSEPEVRIPENNPVKLSC.        (SEQ ID NO: 1)
```

Another preferred F11R-antagonist peptide of the present invention is a sequence within the first Ig fold of the F11R structure:KSVTREDTGTYTC (SEQ ID NO: 4).

Homologs, analogs and fragments of these peptides are also contemplated by the present invention which maintain F11R-antagonist activity in a mammal, particularly humans.

Another aspect of the present invention provides methods of interfering is with, blocking or otherwise preventing the interaction or binding of platelets to endothelial cells via F11R by employing the F11R-antagonists contemplated by the present invention.

The present invention also provides compositions for the treatment of F11R-mediated disorders such as thrombosis, atherosclerosis, plaque formation, heart attacks, stroke and all other clinical disorders involving thrombus formation, in animals, including humans and includes methods of treating such disorders. The present invention is also directed to the treatment and prevention of excessive bleeding following a wound injury and inflammatory diseases of the nervous system. The compositions include at least one of the F11R-antagonists, preferably at least one F11R peptide antagonist according to the present invention, admixed with a pharmaceutically acceptable carrier.

In accordance with the present invention, the protein F11R serves a significant role in the adhesion of platelets to inflamed endothelial cells. The present invention has identified that the activity of F11R is critical for initiating the formation of platelet plaques in blood vessels and for the formation of thrombi. Thus, any agents, chemicals or drugs that inhibit the action of F11R (named here collectively: F11R-antagonists) will serve as powerful inhibitors of thrombus development in the circulation. Accordingly, the present invention provides F11R-antagonists as drugs useful for the prevention and treatment of thrombosis, atherosclerosis, plaque formation, posttransfusion purpura, acute and chronic immunothrombocytopenia, acquired disorders of platelet function, myeloproliferative disorders, uremia, liver disease, cardiopulmonary bypass, various types of thrombosis inflammatory thrombosis, peripheral vein thrombosis, coronary artery thrombosis and other arterial thrombosis, atherosclerosis, disorders of angiogenesis, cancer growth and metastasis, and all other human disorders that involve angiogenesis and/or thrombus formation.

One aspect of the invention is directed to methods of identifying a compound which prevents the adhesion of platelets to endothelial cells and that inhibits platelet aggregation, also referred to as "F11R-antagonists".

The term "compound" is taken to include both organic compounds such as peptides, as well as inorganic compounds such as ion chelators or opiates. Antibodies, e.g., polyclonal or monoclonal antibodies directed against F11R, the Fab, Fab', F(ab')$_2$ fragments of such antibodies, as well as single-chain anti-F11R antibodies can also be considered as compounds useful in the present methods.

Other preferred compounds include chemical compounds that can be derived from the knowledge of the sequence of the F11R, from each of the above sequences (i.e. SEQ ID NOS: 1-7) and from the combination of the sequences together. These include linear sequences, cyclic sequences, annealing of the peptides together (preferably SEQ ID NOS: 1 and 4), and any other possible derivations using standard peptide chemistry techniques. In one embodiment the present invention contemplates any compound whose structure is based on the interaction of peptides 1 and 4 (SEQ ID NOS. 1 and 4), which form the binding site of the mature human platelet F11R.

As used herein a "mimetic" or "peptidomimetic" of a compound's functional site refers to a compound in which chemical structures of protein or peptide sequences necessary for functional activity of a compound's functional site have been replaced with other chemical structures that mimic the conformation of the functional site. An example of a peptidomimetic contemplated by the present invention includes a compound (e.g. a small organic molecule) including portions with residues which interact sterically with the binding site of the F11R molecule. In accordance with the present invention, F11R peptidomimetic drugs can be designed on the basis of, for example, peptides having SEQ ID NOs. 1 and 4 and the tertiary structure of the binding site of F11R, including parts of the protein containing these sequences. Such peptidomimetic drugs with structural relationships analogous to that observed between morphine, enkephalins and beta-endorphins, are suitable as therapeutic agents. The design and synthesis of peptidomimetic molecules continues to be at the forefront of drug design and discovery and many peptidomimetic frameworks and methods for their synthesis have been developed (Babine, R. E.; Bender, S. L., *Chem. Rev.*, 97:1359, 1997; Hanessian, S.; et al., *Tetrahedron*, 53:12789, 1997; Fletcher, M. D.; Cambell, M. C., *Chem. Rev.*, 98:763, 1998), these teachings are incorporated herein by reference.

The peptidomimetics in accordance with the present invention can be developed, for example, with the aid of computerized molecular modeling. In a preferred embodiment, the present invention provides a pharmaceutical composition comprising SEQ ID NO.: 1 or SEQ ID NO. 4 wherein SEQ. ID. NO.: 1 or SEQ ID NO. 4 comprises peptidomimetics that are capable of specific binding with the F11R binding site. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biochemical property or pharmacological activity), such as SEQ. ID. NO.: 1 or SEQ ID NO.:4, but have one or more peptide linkages optionally replaced by a linkage selected from the group consisting of: —CH.sub.2-

NH—, —CH.sub.2S—, —CH.sub.2-CH.sub.2-, —CH.dbd.CH—(cis and trans), —COCH.sub.2-, —CH(OH)CH.sub.2-, and —CH.sub.2SO—, by methods known in the art and further described in the following references: Spatola, A. F. in "Chemistry and Biochemistry of Amino Acids, Peptides, and Proteins," B. Weinstein, eds, Marcel Dekker, New York, p. 267 (1983); Spatola, A. F., *Vega Data* (March 1983), Vol. 1, Issue 3, "Peptide Backbone Modifications" (general review); Morley, J. S., *Trends Pharm Sci* (1980) pp. 463-468 (general review); Hudson, D. et al., (1979) *Int J Pept Prot Re* 14:177-185 (—CH.sub.2NH—, —CH.sub.2-CH.sub.2-); Spatola, A. F. et al., (1986) Life Sci 38:1243-1249 (—CH.sub.2-S); Hann, M. M., (1982) *J Chem Soc Perkin Trans I* 307-314 (—CH.dbd.CH—, cis and trans); Almquist, R. G. et al., (1980) *J Med Chem* 23: 1392-1398 (—COCH.sub.2-); Jennings-White, C. et al., (1982) *Tetrahedron Lett* 23:2533 (—COCH.sub.2-); Szelke, M. et al., European Appln. EP 45665 (1982) CA. 97:39405 (1982) (—CH(OH)CH.sub.2-); Holladay, M. W. et al., (1983) *Tetrahedron Lett* 24:4401-4404 (—C(OH)CH.sub.2-); and Hruby, V. J., (1982) *Life Sci* 31:189-199 (—CH.sub.2-S—); each of which is incorporated herein by reference.

In another embodiment, a particularly preferred non-peptide linkage is —CH.sub.2NH—. Such peptidomimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptidomimetics are possible. For example, cyclic peptides, in which the necessary conformation for binding is stabilized by nonpeptides, are specifically contemplated. U.S. Pat. No. 5,192,746 to Lobl, et al., U.S. Pat. No. 5,169,862 to Burke, Jr., et al, U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred, et al., (*J. Med. Chem.* 37:3882 (1994)) describe nonpeptide antagonists that mimic the peptide sequence. Likewise, Ku, et al., (*J. Med. Chem.* 38:9 (1995)) give further elucidation of the synthesis of a series of such compounds. Derivatives of e.g. SEQ. ID. NO.: 1 or SEQ ID NO.: 4 can be produced using recombinant nucleic acid molecule techniques.

Modifications to a specific peptide may be deliberate, as through site-directed mutagenesis and amino acid substitution during biosynthesis, or may be accidental such as through mutations in hosts, which produce the peptide. Peptides including derivatives can be obtained using standard mutagenesis techniques such as those described in Sambrook et al., Molecular Cloning, Cold Spring Harbor Laboratory Press (1989). For example, Chapter 15 of Sambrook describes procedures for site-directed mutagenesis of cloned DNA. Derivatives of SEQ. ID. NOs.: 1 and 4 include, but are not limited by modification occurring during or after translation, for example, by phosphorylation, glycosylation, crosslinking, acylation, proteolytic cleavage, linkage to a therapeutic protein, an antibody molecule, membrane molecule or other ligand (see Ferguson et al., 1988, *Annu. Rev. Biochem.* 57:285-320). Specific types of genetically produced derivatives also include, but not limited by amino acid alterations such as deletions, substitutions, additions, and amino acid modifications. A "deletion" refers to the absence of one or more amino acid residue(s) in the related peptide. An "addition" refers to the presence of one or more amino acid residue(s) in the related peptide. Additions and deletions to a peptide may be at the amino terminus, the carboxy terminus, and/or internal, can be produced by mutation in e.g., SEQ. ID. NO.: 1 encoding DNA and/or by peptide post-translation modification. Amino acid "modification" refers to the alteration of a naturally occurring amino acid to produce a non-naturally occurring amino acid. Analogs of e.g. SEQ. ID. NO.: 1 with unnatural amino acids can be created by site-specific incorporation of unnatural amino acids into polypeptides during the biosynthesis, as described in Christopher J. Noren, Spencer J. Anthony-Cahill, Michael C. Griffith, Peter G. Schultz, 1989 *Science,* 244:182-188. A "substitution" refers to the replacement of one or more amino acid residue(s) by another amino acid residue(s) in the peptide. Mutations can be made in e.g., SEQ. ID. NO.: 1 encoding DNA such that a particular codon is changed to a codon, which codes for a different amino acid. Such a mutation is generally made by making the fewest nucleotide changes possible. A substitution mutation of this sort can be made to change an amino acid in the resulting peptide in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting peptide. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids. Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp). Derivatives can contain different combinations of alterations including more than one alteration and different types of alterations.

The ability of the derivative to retain some activity can be measured using techniques described herein and/or using techniques known to those skilled in the art for measuring the F11R receptor binding activity. "Derivatives" of e.g., SEQ. ID. NO.: 1 are functional equivalents having similar amino acid sequence and retaining, to some extent, the activities of SEQ. ID. NO.: 1. By "functional equivalent" is meant the derivative has an activity that can be substituted for the activity of SEQ. ID. NO.: 1. Preferred functional equivalents retain the full level of F11R-binding activity as measured by assays known to these skilled in the art. Preferred functional equivalents have activities that are within 1% to 10,000% of the activity of e.g., SEQ. ID. NO.: 1, more preferably between 10% to 1000%, and more preferably within 50% to 200%. Derivatives have at least 50% sequence similarity, preferably 70%, more preferably 90%, and even more preferably 95% sequence similarity to SEQ. ID. NO.: 1. "Sequence similarity" refers to "homology" observed between amino acid sequences in two different polypeptides, irrespective of polypeptide origin. A "residue" refers to an amino acid incorporated in the peptide by an amide bond, for example. Approaches to designing peptide mimetics are known in the art. For example, see Farmer, P. S. in *Drug Design* (E. J. Ariens, ed). Academic Press, New York, 1980, vol. 10, pp. 119-143; Ball J. B. and Alewood, P. F. (1990) *J. Mol. Recognition* 3:55, Morgan B. A. and Ganor, J. A. (1985) *Ann. Rev. Med Chem.* 24:243 and Freidinger R. M. (1989) *Trends Pharmacol. Sci:* 10:270, incorporated herein by reference. In one embodiment, the present invention contemplates all peptidomimetics which can be designed based on the knowledge of the sequence and of the three-dimensional structure of the F11R molecule of the invention including but not limited to all mimetic compounds which can be conventionally synthesized by an ordinarily skilled chemist to bind to, antagonize, act as an agonist, inhibit, promote, block, or otherwise functionally interact with the binding site of the F11R as illustrated in FIG. 1, for example.

Most preferred compounds of the present methods are peptides which are made to resemble the monoclonal antibody F11 ("M.Ab.F11") binding site on platelets.

"F11R" refers to a receptor protein on the surface of human platelets as a target for a stimulatory M.Ab.F11 "F11R" is also referred to as human ortholog of the murine protein called junctional adhesion molecule (JAM), specifically named JAM-1 and JAM-A. "F11R" is depicted in FIG. 1 as a backbone structure in its entirety including the extracellular, soluble domain, consisting of two Ig-folds, a transmembrance domain and a short cytoplasmic portion, on both human platelets and endothelial cells.

"F11R antagonists" and "F11R antagonist peptides" further refers to any compound that can bind to the active site of the F11R protein, specifically, but not limited to a pocket formed by the N-terminal 23 amino acid region and 13 amino acid region in the first Ig fold. By such binding, the action of F11R is inhibited, i.e. alignment of platelets and endothelial cells in F11R-mediated trans-homophilic interaction through the steric pocket, as depicted in FIGS. 1-2, is blocked so that platelet aggregation or thrombosis, atherosclerosis, heart attacks, strokes, and all other human disorders that involve thrombus formation, can be prevented or treated. By "F11R antagonist peptide" is also meant a peptide that inhibits, suppresses or causes the cessation of at least one F11R mediated biological activity by e.g. interfering with or otherwise preventing the interaction or binding of platelets to endothelial cells and thereby inhibit platelet aggregation or interfering with the role of some protein in angiogenesis and thus preventing the growth of tumors.

In accordance with the present invention, two peptide sequences of the F11R have been determined the sequences correspond to (the N-terminus SVTVHSSEPEVRIPEN-NPVKLSC (SEQ ID NO: 1), and the first Ig fold sequence KSVTREDTGTYTC (SEQ ID NO: 4). The peptide sequences of the present invention inhibit the adhesion of platelets to endothelial cells and inhibit platelet aggregation.

As used herein, "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present invention. According to the present invention, preferred F11R antagonists include peptides (referred to herein as "F11R antagonist peptides") and antibodies. Additionally, analogs, homologs and fragments of the novel peptides provided herein are included within the scope of the term "F11R antagonist peptide".

By "homologs" is meant the corresponding peptides from F11R proteins of other mammalian species substantially homologous at the overall protein (i.e., mature protein) level to human F11R, so long as such homologous peptides retain the F11R antagonist activity.

By "analogs" or "F11R-Antagonist Peptide Analysis" is meant peptides which differ by one or more amino acid alterations, which alterations, e.g., substitutions, additions or deletions of amino acid residues, do not abolish the F11R antagonist properties of the relevant peptides. Thus, an analog can comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cyteine, glutamine, glutamic acid, lysine and/or a polar residue for a non-polar residue.

The phrase "conservative substitution" also includes the use of chemically derivatized residues in place of a non-derivatized residues as long as the peptide retains the requisite F11R antagonist, inhibition properties as conventionally measured. Analogs also include the presence of additional amino acids or the deletion of one or more amino acids which do not affect F11R-mediated biological activity. For example, analogs of the subject peptides can contain an N- or C-terminal cysteine, by which, if desired, the peptide can be covalently attached to a carrier protein, e.g., albumin. Such attachment, it is believed, will minimize clearing of the peptide from the blood and also prevent proteolysis of the peptides. In addition, for purposes of the present invention, peptides containing D-amino acids in place of L-amino acids are also included in the term "conservative substitution". The presence of such D-isomers can help minimize proteolytic activity and clearing of the peptide.

The term "fragment" refers to any subject peptide having an amino acid sequence shorter than that of any peptide depicted in SEQ ID NOS: 1-5 and 7 and which fragment retains the F11R-mediated antagonist activity of the subject peptides.

The practice of the present invention employs, unless otherwise indicated, conventional techniques of synthetic organic chemistry, protein chemistry, molecular biology, microbiology, and recombinant DNA technology, which are well within the skill of the art. These techniques are applied in connection with peptide synthesis, recombinant production of peptides and peptide mutagenesis, for example. Such techniques are explained fully in the literature. See e.g., Scopes, R. K., *Protein Purification Principles and Practices*, 2d ed. (Springer-Verlag. 1987), *Methods in Enzymology* (M. Deutscher, ed., Academic Press, Inc. 1990), Sambrook, et al.,

*Molecular Cloning: A laboratory Manual,* 2d ed., (Cold Spring Harbor Press, Cold Spring Harbor, N.Y., 1989), *Handbook of Experimental Immunology,* Vols. I-IV (D. M. Weir and C. C. Blackwell, eds., 1986, Blackwell Scientific Publications), House, *Modern Synthetic Reactions,* 2d ed, (Benjamin/Cummings, Menlo Park, Cal., 1972).

The peptides of the present invention, homologs, analogs and fragments thereof can be synthesized by a number of known techniques. For example, the peptides may be prepared using the solid-phase synthetic technique initially described by Merrifield, in J. Am. Chem. Soc. 85:2149-2154 (1963). Other peptide synthesis techniques can be found in M. Bodanszky, et al. *Peptide Synthesis,* John Wiley & Sons, 2d Ed., (1976) and other references readily available to those skilled in the art. A summary of polypeptide synthesis techniques can be found in J. Stuart and J. D. Young, *Solid Phase Peptide Synthesis,* Pierce Chemical Company, Rockford, Ill., (1984). Peptides may also be synthesized by solution methods as described in *The Proteins,* Vol. II. 3d Ed., Neurath, H. et al., Eds., p. 105-237, Academic Press, New York, N.Y. (1976). Appropriate protective groups for use in different peptide syntheses are described in the above-mentioned texts as well as in J. F. W. McOmie, *Protective Groups in Organic Chemistry,* Plenum Press, New York, N.Y. (1973). The peptides of the present invention can also be prepared by chemical or enzymatic cleavage from larger portions of the F11R molecule or from the entire F11R molecule.

Additionally, the peptides of the present invention can also be prepared by recombinant DNA techniques (see e.g. *Current Protocols in Molecular Cloning* Ausubel et al., 1995, John Wiley & Sons, New York); Sambrook et al., 1989, *Molecular Cloning: A Laboratory Manual,* Second Edition, Cold Spring Harbor Laboratory Press, New York; Coligan et al. *Current Protocols in Immunology,* John Wiley & Sons Inc., New York, N.Y. (1994)). The skilled artisan understands that any of a wide variety of expression systems can be used to provide the recombinant peptides of the present invention. The precise host cell used is not critical to the invention. The F11R antagonist peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in *Cloning Vectors: A Laboratory Manual* P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject F11R antagonist peptide. The present invention also contemplates a deoxyribonucleic acid (DNA) molecule or segment that defines a gene coding for, i.e., capable of expressing, a subject peptide or a subject chimeric peptide from which a peptide of the present invention can be enzymatically or chemically cleaved.

DNA molecules that encode peptides of the present invention can be synthesized by chemical techniques, for example, the phosphotriester method of Matteuccie, et al., *J. Am. Chem. Soc.* 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments. Consistent with the observed properties of the peptides of the invention, the present peptides can be used to inhibit, suppress, or cause the cessation of at least one F11R-mediated biological activity. F11R functions in the biochemical events associated with platelets aggregation and adhesion of platelets to endothelial cells. Accordingly, the present invention contemplates methods to block, interrupt or otherwise prevent the association of platelets to endothelial cells and thereby effectively treat or prevent F11R-cell associated disorders such as thrombosis, for example.

F11R-mediated disorders such as, for example, thrombosis, atherosclerosis, heart attacks and strokes are F11R-dependent therefore treatable with the F11R antagonists, preferably F11R antagonist peptides or peptidomimetics of the present invention. Other F11R related diseases are also contemplated by the present invention.

In another embodiment of the present invention, one or more F11R antagonists, e.g., F11R antagonist peptides, peptidomimetics or antibodies, are included in pharmaceutical compositions.

Preferably, compositions containing the F11R antagonist peptides or peptidomimetics of the present invention are administered intravenously to inhibit, suppress, or cause the cessation of at least one F11R-mediated biological activity. When administered intravenously, the peptide compositions can be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present invention include, but are not limited to anti-F11R antibodies, NSAIDS, steroids, or cyclosporin-A. When employed together with F11R antagonists, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride can be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides or peptidomimetics of the invention are administered orally, the pharmaceutical compositions thereof containing an effective dose of the peptide can also contain an inert diluent, as assimilable edible carrier and the like, be in hard or soft shell gelatin capsules, be compressed into tablets, or can be in an elixir, suspension, syrup or the like.

The subject peptides or peptidomimetics are thus compounded for convenient and effective administration in pharmaceutically effective amounts with a suitable pharmaceutically acceptable carrier in a therapeutically effective dose.

The peptides and peptidomimetics should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

The peptides and peptidomimetics can be administered in a manner compatible with the dosage formulation and in such amount as well be therapeutically effective. Systemic dosages depend on the age, weight and conditions of the patient and on the administration route. For example, a suitable dose for the administration to adult humans ranges from about 1 mg/kg of body weight about 10 mg per kilogram of body weight. The present invention also contemplates that the peptide or peptidomimetic compositions can be suitably coated on stents, lines, and tubes with a therapeutically effective amount of the peptide which amount can be readily determined by the skilled practitioner.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions can be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like can be used. In addition, carriers such as liposomes and microemulsions can be used.

In a further aspect of the present invention, the pharmaceutical compositions of the present invention are employed for the treatment of F11R mediated pathological disorders. Thus, the present invention provides methods of treating an F11R mediated disorder in a subject by administering a therapeutically effective amount of a pharmaceutical composition of the present invention.

The term "therapeutically effective amount" means the dose required to treat an F11R-mediated disorder.

By "an F11R-mediated disorder" is meant a pathological disorder, the onset, progression or the persistence of the symptoms of which requires the participation of F11R molecules. Particularly, F11R-mediated disorders contemplated by the present invention include thrombosis, atherosclerosis, heart attacks and strokes. In addition, the inventors have determined that collagen-induced platelet aggregation and secretion can be blocked completely by the F11R peptides of the present invention.

Accordingly, "an F11R-mediated disorder" also contemplates excessive bleeding as may occur following a wound injury. Furthermore, and in accordance with the present invention "an F11R-mediated disorder" can include inflammatory diseases of the nervous system.

The term "treatment" or "treat" refers to effective inhibition, suppression or cessation of the F11R activity so as to prevent or delay the onset, retard the progression or ameliorate the symptoms of the disorder.

The term "subject" refers to any mammalian subject. Preferably, the subject is a human.

The present invention thus provides methods of interfering with, blocking or otherwise preventing the interaction or binding of platelets with endothelial cells by employing the F11R antagonists contemplated by the present invention.

The F11R antagonist peptides of the present invention (or homologs, analogs or fragments) can be used to raise single-chain antibodies (SAb) or humanized monoclonal antibodies useful in the invention. The peptides can be coupled to a carrier protein such as KLH as described in Ausubel et al. (1989) *Current Protocols in Molecular Biology*, John Wiley & Sons, New York. The KLH-antagonist peptide is mixed with Freund's adjuvant and injected into guinea pigs, rats, donkeys and the like or preferably into rabbits. Antibodies can be purified by peptide antigen affinity chromatography.

A single-chain antibody (SAb) is created by fusing together the variable domains of the heavy and light chains using a short peptide linker, thereby reconstituting an antigen binding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. (1990) *J. Biol. Chem.*, 265:18615; Chaudhary et al. (1990) *Proc. Natl. Acad. Sci.*, 87:9491; U.S. Pat. No. 4,946,778 to Ladner et al.; and U.S. Pat. No. 5,359,046 to Capon et al.

Monoclonal antibodies can be prepared using F11R antagonist peptides and standard hybridoma technology (see e.g. Kohler et al., (1975) Nature 256:495; Hammerling et al., (1981) *In Monoclonal Antibodies and T Cell Hybridomas*, Elsevier, N.Y.). For example, monoclonal antibodies to F11R antagonist peptides (homologs, analogs or fragments thereof) can be raised in Balb/C or other similar strains of mice by immunization with purified or partially purified preparations of F11R antagonist peptides. The spleens of the mice can be removed, and their lymphocytes fused to a mouse myeloma cell line. After screening of hybrids by known techniques, a stable hybrid will be isolated that produces antibodies against F11R antagonist peptides. The monoclonal antibody can be examined for its ability to inhibit the biological activity of F11R, e.g. platelet aggregation. Once produced, monoclonal antibodies are tested for specific F11R recognition by Western blot or immunoprecipitation analysis (by methods described in Ausubel et al., supra). Antibodies which antagonize F11R/platelet aggregation are considered to be useful antagonists in the invention.

The monoclonal antibodies of the present invention can be humanized to reduce the immunogenicity for use in humans. One approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86101533, (published Mar. 13, 1986); Kudo et al., European Patent Application 184187 published Jun. 11, 1986); Robinson et al., International Patent Publication #PCT/US86/02269 published 7 May 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

The invention is further illustrated by the following specific examples which are not intended in any way to limit the scope of the invention.

Example 1

Human platelets. Whole blood was collected into the anticoagulant ACD (pH 4.6), as detailed (Kornecki et al. (1990) *J. Biol. Chem.*, 265:10042-10048, incorporated herein by reference). Platelets were washed and isolated by differential centrifugation, and resuspended in a Tyrode-albumin (0.35%) solution buffered with 11.9 mM sodium bicarbonate (pH 7.35) in the presence of apyrase, heparin, and $PGE_1$ (Id.). Final platelet suspensions did not contain any inhibitors. Platelet aggregation was measured in a Chronolog Whole Blood Lumi-Aggregometer (Chronolog Corp. Havertown, Pa.). Potentiation of platelet aggregation was measured by adding a mixture of two platelet agonists, each at a subthreshold concentration that did not induce any platelet aggregation. The lowest concentration of each agonist which caused platelet aggregation was determined in these experiments for each donor on the day of blood collection.

Immunoblotting. Polyacrylamide gel electrophoresis, immunoblotting of transferred proteins onto nitrocellulose strips, and detection using ECL chemluminescence were performed as detailed (Id.).

Antibodies. Monoclonal antibody M.Ab.F11 (IgG1 isotype) was affinity-purified as described (Id.). Histidine antibody was obtained from InVitrogen (Carlsbad, Calif.).

Construction of the plasmid pcDNA3.1/F11R. A 726-base-pair fragment (nucleotide-6 till +720) was amplified by PCR using a human F11 receptor cDNA as a template (Sobocka et al. (1997) *Blood,* 90(10); Supp. 1, Part 2, 2996a, incorporated herein by reference) utilizing the forward primer [GCGG-GATCCATCGCGATGGGGACAAAGGCG (SEQ ID NO: 8)], and the reverse primer [CCGACCTCGAGCGGCATTC-CGCTCCACAGCTTCCAT (SEQ ID NO: 9)] (bases in bold represent BamHI and XhoI sites), respectively. This PCR fragment encodes amino acids ser-1 to asn-208 of F11R, and excludes the C-terminal transmembrane and cytoplasmic domains. The 726-base-pair PCR-product was subcloned into plasmid pcDNA3.1/Myc-His (+) C (Invitrogen, Carlsbad, Calif.) using BamHI and XhoI to yield pcDNA3.1/F11R. Transcription of the F11R in this plasmid is under the control of CMV immediate-early promoter. The construct pcDNA3.1/F11R was verified by sequencing and fine restriction mapping prior to its use in expression studies in COS-7 cells.

Recombinant DNA methods. *E. coli* transformation, plasmid DNA isolation, restriction analysis, extraction of DNA from agarose gells and ligation of insert into pcDNA3.1/myc-His(+)C vector were carried out as described (Sambrook et al. *Molecular Cloning: A Laboratory Manuel $2^{nd}$ Ed. Cold Spring Harbor Laboratory*, is Cold Spring Harbor, N.Y. 1989, incorporated herein by reference). Plasmids were isolated from *E. coli* DH5α (Life Technologies, Grand Island, N.Y.) using Qiaprep columns (Qiagen, Valencia, Calif.). DNA restriction fragments were separated by agarose gel eletrophoresis and isolated with the QIAquick Gel extraction kit (Qiagen). PCR was performed using the Perkin Elmer Gene Amp 2400PCR System. DNA sequencing was performed by PCR-cycle sequencing using ABI PRISM Dye Terminator Cycle Sequencing Kit from Perkin Elmer (Foster City, Calif.) and the ABI Prism 377 DNA Squencer. Computer analysis of sequence data was performed with the Biology WorkBench, release 3.2.

Transfection of COS-7 cells. COS-7 cells were grown in DMEM/10% FBS (Cellgro Mediatech, Inc.) and 1% antimycotic (Life Technologies), at 37° C./5% $CO_2$. Cells (about 50% confluency), plated in a 75 mm flask, were used for transfection one day later. The plasmid pcDNA3.1/F11R (10 µg) was transfected into cells using 30 µl of FuGENE-6 (Roche Diagnostics). Cells were maintained at 37° C./5% $CO_2$ in 7 ml complete medium. Cells were also treated with FuGENE-6 alone as controls. Total RNA was isolated (RNeasy Mini Kit, Qiagen) and used for subsequent RT-PCR. RNA (2 µg) was used for reverse transcription (Omniscript Reverse Transcriptase, Omniscript RT Kit, Qiagen). Half of the reaction mixture was used to amplify F11R in a 35-cycle PCR using the specific F11R primers as detailed previously (Sobocka, supra). PCR cycling was as follows: 94° C. for 5 min followed by 35 cycles of 94° C. for 45 sec, 55° C. for 45 sec, 72° C. for 2 min and 94° C. for 2 min. A 726-bp fragment was obtained only from pcDNA3.1/F11R transfected cells. Conditioned media, collected 72 h posttransfection, were pooled and passed twice over a M.Ab.F11-immunoaffinity column. After washing of the affinity column, the bound sF11R was eluted by use of 50 mM diethylamine (pH 11.5), fractions were collected into 1 M Tris-HCl buffer (pH 8.0) and immediately dialysed against 10 mM Tris-HCl buffer (pH 7.4). The sF11R solution was concentrated 5× by Centricon YM-10 (Bedford, Mass.), and stored frozen at −20° C.

Synthesis of F11R-peptides. Five F11R peptides (95% pure) were synthesized (New England Peptides, Inc., Fitchburg, Mass.). The sequence of amino acids in these peptides and their location within the F11R molecule are shown in Table. Their mass was determined by MALDI-TOF DE mass spectrometry.

TABLE 1

| Peptide name | PEPTIDE SEQUENCE | | |
|---|---|---|---|
| F11R-peptide 1 | *SVTVHSSEPEVRIPENNPVKLSC 1----------------------23 | (SEQ ID NO: 1) | |
| F11R-peptide 2 | SYEDRVTFLPTGITFKSVTRED 55--------------------76 | (SEQ ID NO: 2) | |
| F11R-peptide 3 | WKFDQGDTTRLVEYNNKITASY 35--------------------56 | (SEQ ID NO: 3) | |
| F11R-peptide 4 | KSVTREDTGTYTC 70-----------82 | (SEQ ID NO: 4) | |
| F11R-peptide 5 | EQDGSPPSEYTWFKD 128------------142 | (SEQ ID NO: 5) | |

The amino acid numbers refer to the sequence of the mature platelet cell surface F11 receptor and of the recombinant protein, sF11R, which does not include the leader peptide sequence.
*In accordance with the present invention, ser-1 is the first amino acid that follows the 27 amino acid leader peptide sequence of the nascent protein (Sobocka et al. (2000) Blood 95:2600-2609).

Platelet adhesion to an immobilized matrix. An adhesion assay, based on the determination of cell-derived protein using Bicinchoninic Acid (BCA) protein assay (Tuszynski et al. (1990) Anal. Biochem 184:189-191, incorporated herein by reference), was used for platelet adhesion to immobilized M.Ab.F11. Wells of a 96-well plate (Nunc-Immuno™ Plate, MaxiSorp™ Surface, flat bottomed) were incubated overnight at 4° C. with 150 ml of a 1 mg/ml solution of M.Ab.F11. Wells were aspirated, washed, treated with TBS/1% BSA for 1 h at 37° C., and washed with TBS/0.1 mM $MnCl_2$/0.1 mM $CaCl_2$. Isolated platelet suspensions (1001) ($3\times10^8$/ml) were added and plates were incubated at 37° C. for 90 min. Total platelet-associated protein was determined by dissolving the attached platelets directly with 100 µl BCA. Platelets were incubated at 37° C. for 2 h, and absorbance (595 nm) determined (Dynatech Laboratories, Chantilly, Va.).

3D-Structure of humans sF11R. The crystal structure of the external domain of mouse recombinant JAM (Kostrewa et al. (2001) The Embo J. 20:4391-4398, incorporated herein by reference) was used as a template to generate a 3D model of the human recombinant sF11R based on the sequence (Sobocka et al. (2000) Blood 95:2600-2609, incorporated herein by reference) of the mature human platelet F11R (GenBank accession #AF207907).

Example 2

Preparation and use of Recombinant sF11R. A schematic model of the external domain of the F11R protein constructed on the basis of its sequence (Sobocka 2000) is illustrated in FIG. 1. A secreted, recombinant F11R protein (sF11R) was prepared in COS-7 cells which contained only the extracellular portion (amino acids ser-1 to asn-208) of the mature F11R molecule. The transcription of the recombinant sF11R in COS-7 cells was determined by RT-PCR. A 726-base-pair fragment was detected only in pcDNA3.1/F11R transfected cells. (Babinska et al. (2002) Thromb. Haemost 87:712-721, incorporated herein by reference). To determine the expression of sF11R in COS-7 cells, the conditioned media obtained from transfected cells were examined by immunoblotting using both a polyclonal anti-F11R antibody and the monoclonal M.Ab.F11. The sF11R polypeptide was detected in the F11R COS-7 conditioned media obtained from these two separate F11R secreting clones, COS-7 cells which were treated with only Fugene 6 (mock-transfected), or COS-7 cells transfected is with a plasmid lacking F11R DNA, did not secrete sF11R. The sF11R protein was engineered to contain a Histidine tag sequence, and indeed, it was recognized by an anti-His antibody. The use of a control protein (Positope, 53 kD, obtained from InVitrogen) that contains the His tag, confirmed this identification. Finally, sF11R was purified from COS-7 cell media using M.Ab.F11 immunoaffinity chromatography. The purified sF11R was recognized by both the platelet stimulatory monoclonal antibody, M.Ab.F11, and by a polyclonal F11R antibody, directed against the N-terminal amino acids ser-1 to cys-23. The results detailed above demonstrate that transfected COS-7 cells not only synthesize by also secrete sF11R.

Example 3

Figure 3A:
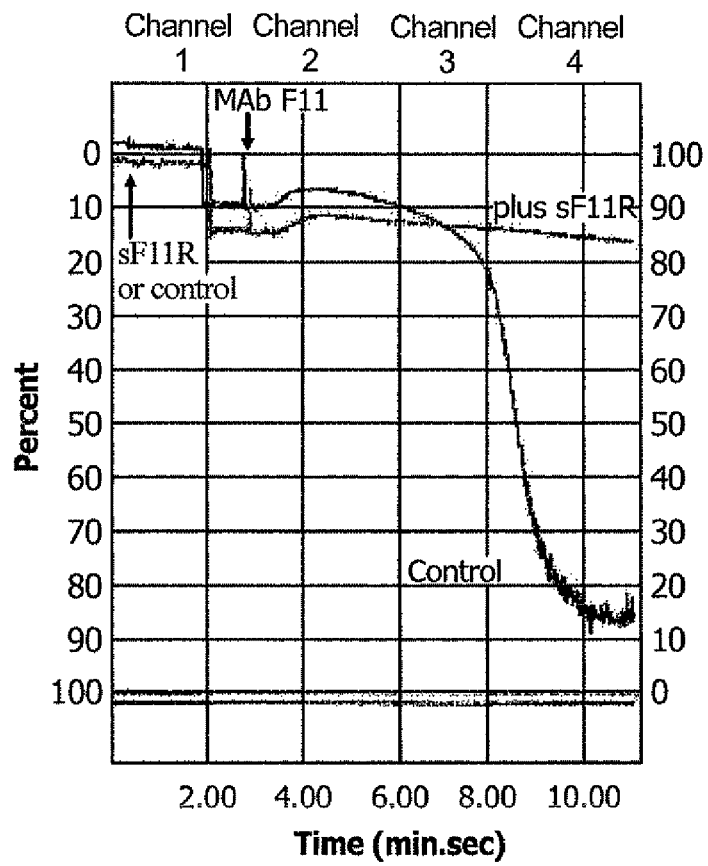
FIG. 3 shows inhibition of M.Ab.F11-induced platelet aggregation by F11R peptides (FIG. 3A); Inhibition of M.Ab.F11 (2.45 µg/ml)-induced platelet aggregation by 50 µM F11R peptide (SEQ ID NO: 1) and by 50 µM F11R peptide (SEQ ID NO: 4) FIG. 3B Control.
Figure 3B:
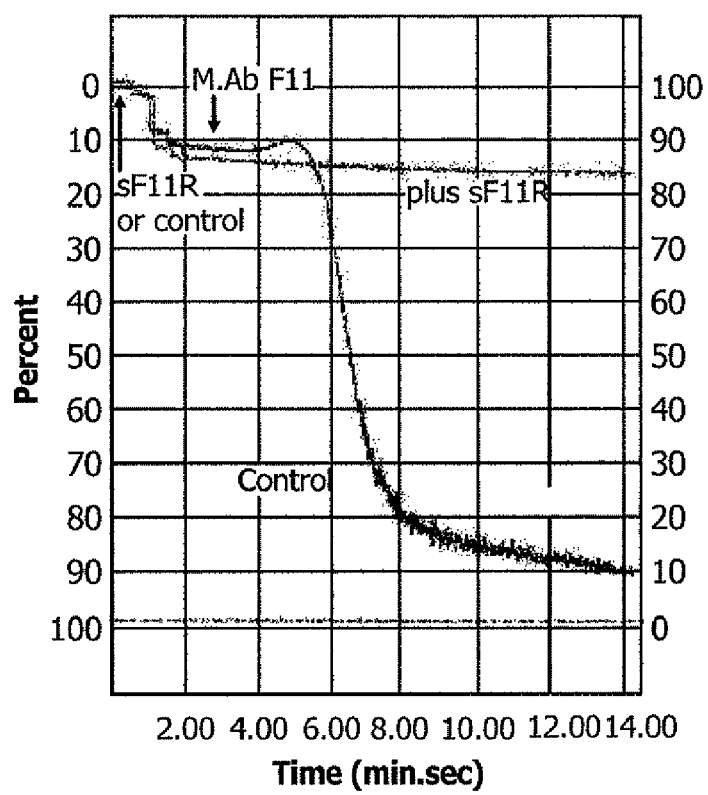
Figure 4A:
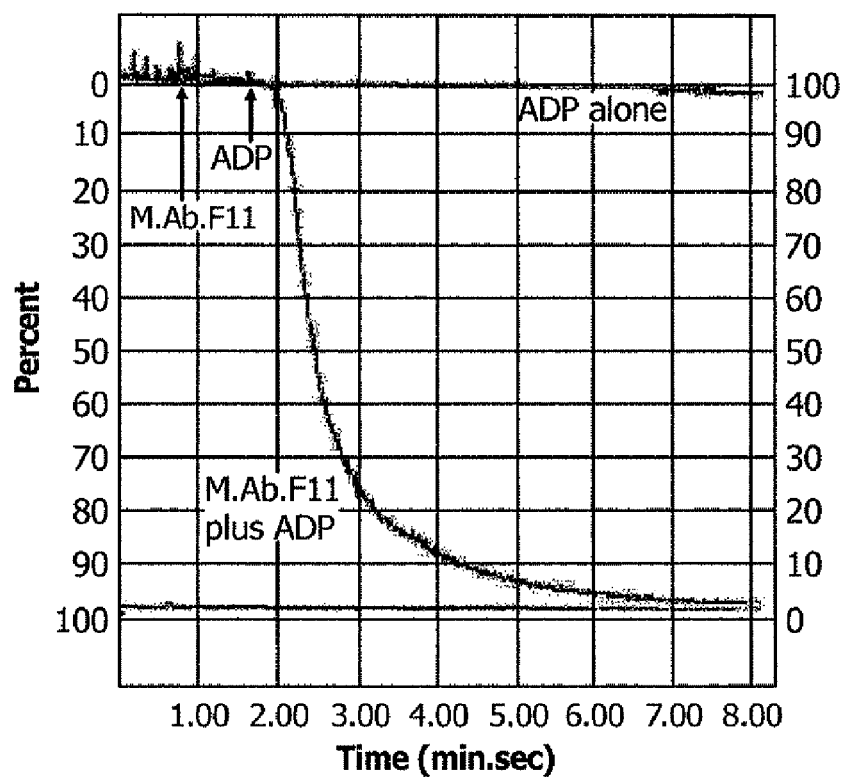
FIGS. 4A-4D show that potentiation of collagen-inducted platelet aggregation by M.Ab.F11 is inhibited by F11R peptides (SEQ ID NOS: 1 and 4).
Figure 4B:
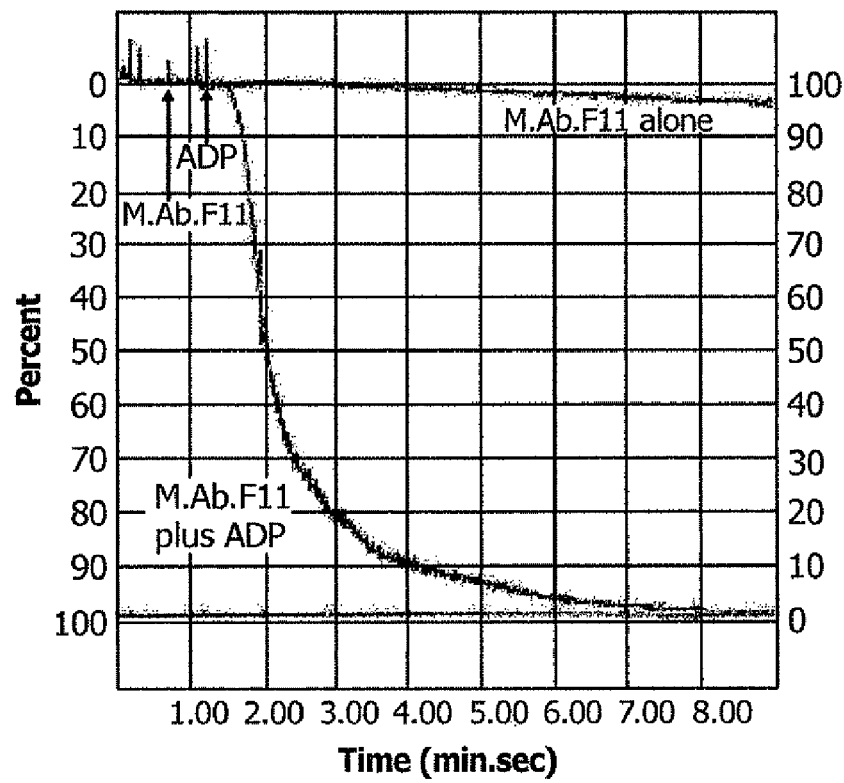
Figure 4C:
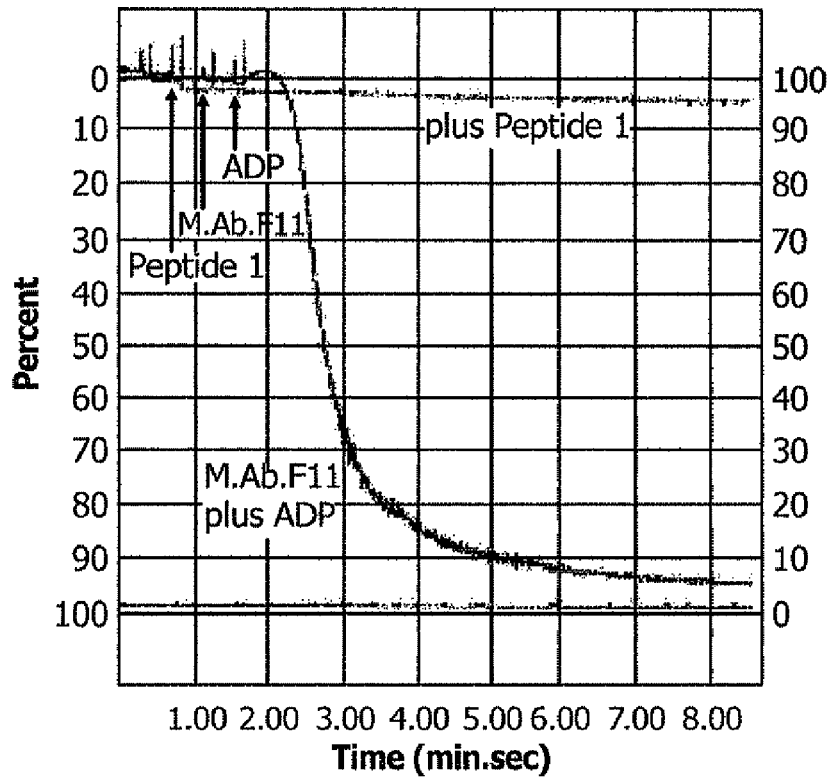
Figure 4D:
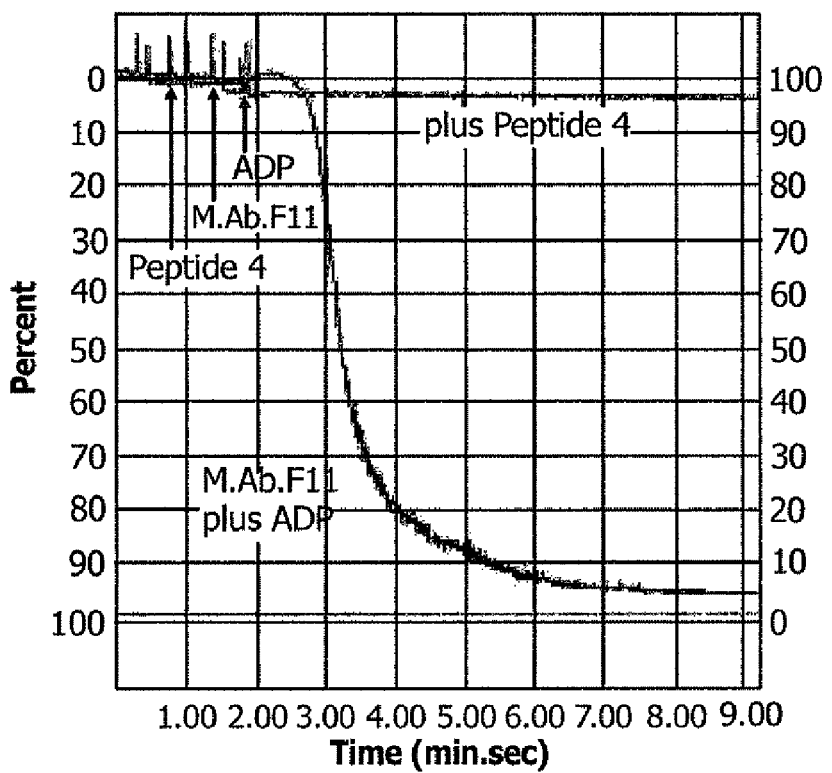

Inhibitory effects of specific F11R-peptides. Synthetic peptides according to published sequences of F11R were prepared. (Naik et al. (1995) Biochem. J, 311:155-162, incorporated herein by reference) (see also Table 1) and used for the identification of domains involved in M.Ab.F11-induced platelet aggregation. As shown in FIG. 3A, peptide 1 (SEQ ID NO: 1) (50 µM) completely inhibited M.Ab.F11-induced platelet aggregation, and aggregation did not ensue when examined even after a 12 h period. In contrast, the addition of 50-500 mM of peptides 2 (SEQ ID NO: 2), 3 (SEQ ID NO: 3), or 5 (SEQ ID NO: 5) (shown in panel C), derived from the F11R sequence (see Table 1), had no inhibitory effects. On the other hand, in addition to peptide 1, peptide 4 (SEQ ID NO: 3) (50 µM), was able to completely block M.Ab.F11-induced platelet aggregation (FIG. 3, panel B).

Example 4

Figure 2A:
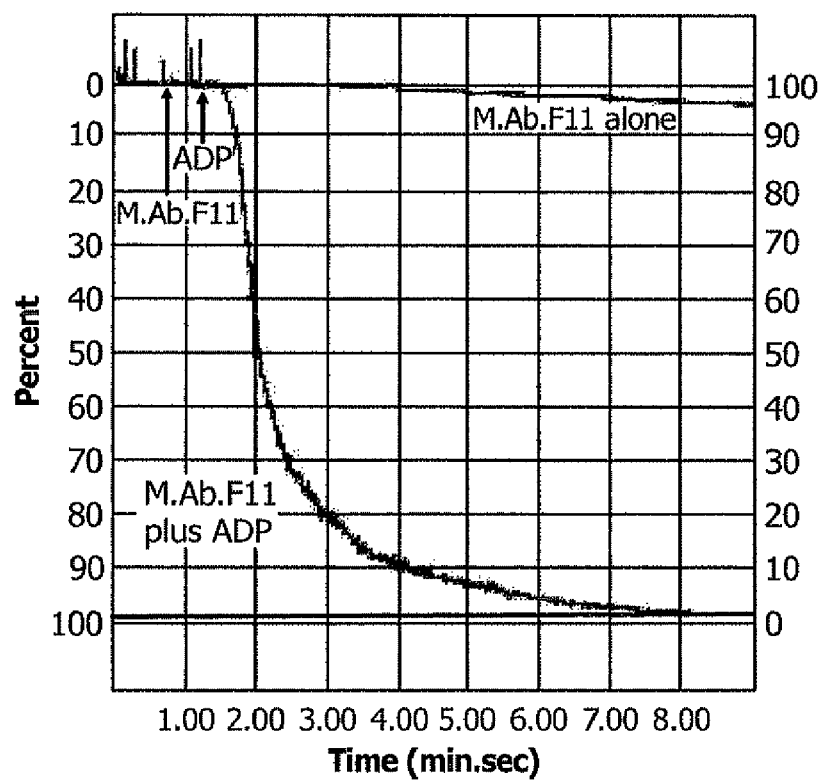
FIG. 2A demonstrates strong potentiation of aggregation using subthreshold levels of M.Ab.F11 (0.3 µg/ml) and ADP (0.5 µM). No aggregation with ADP or M.Ab.F11 alone, when used at low, subthreshold concentrations.
Figure 2B:
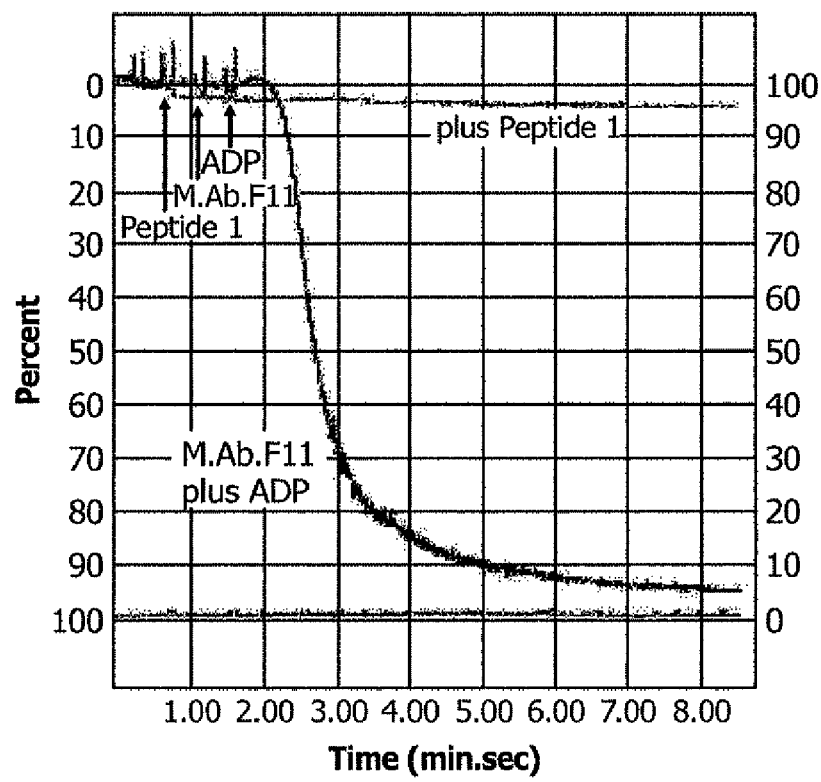
FIG. 2B demonstrates that a subthreshold concentration of M.Ab.F11 (0.3 µg/ml) does not induce platelet aggregation. However, ADP (0.5 µM) plus M.Ab.F11 causes a strong aggregation.
Figure 2C:
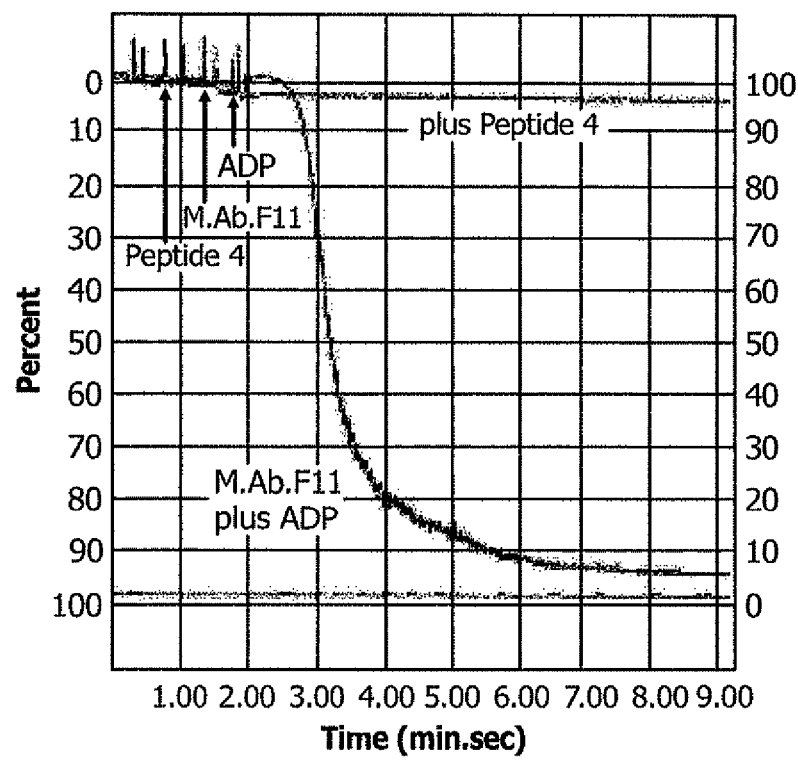
FIG. 2C demonstrates inhibition of the potentiation of aggregation by F11R-peptide (SEQ ID NO: 1). SEQ ID NO: 1 (50 µM) preincubated with platelets for about 30 sec prior to the addition of M.Ab.F11 (0.3 g/ml) followed by the addition of ADP (0.5 µM) inhibited aggregation. Control: aggregation in the absence of SEQ ID NO: 1.
Figure 2D:
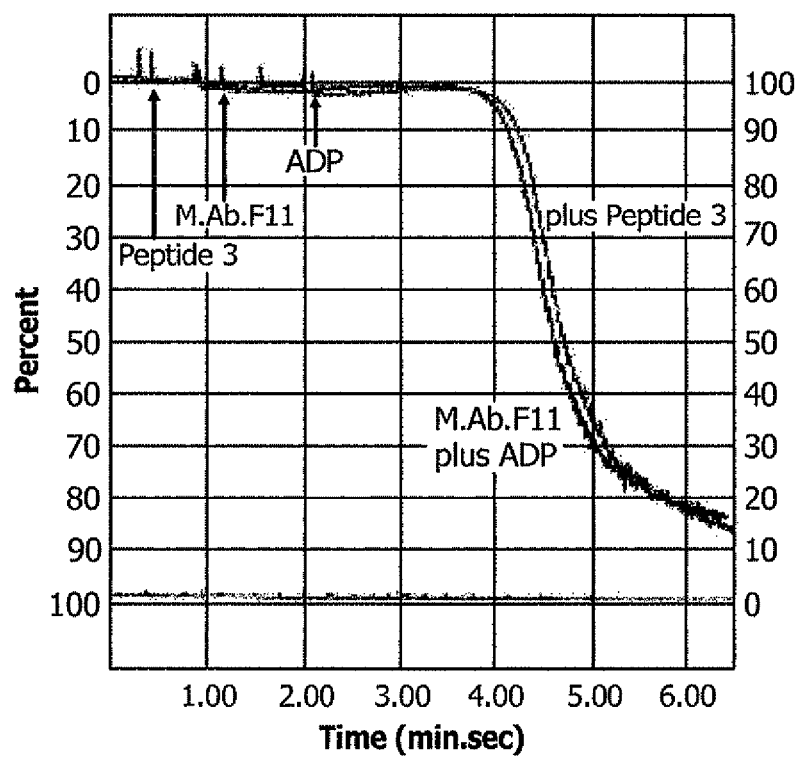
FIG. 2D demonstrates inhibition of the potentiation of aggregation by F11R-peptide (SEQ ID NO: 4). SEQ ID NO: 4 preincubated with platelets for about 42 sec. prior to the addition of M.Ab.F11 (0.3 µg/ml) followed by addition of ADP (0.5 µM) inhibited aggregation. Control: aggregation in the absence of SEQ ID NO: 4.

Potentiation of agonist-induced platelet aggregation by F11R. The presence of low, non-aggregating (sub-threshold) concentrations of the physiological agonist ADP, collagen or thrombin can cause platelet aggregation when added together with non-aggregating concentrations of M.Ab.F11 (Sobocka et al. (1997); Sobocka et al. (1998) PhD Thesis, SUNY Downstate, Brooklyn, N.Y. Jun. 10, 1998, published Sep. 15, 1998; Sobocka et al. 2001, supra, incorporated herein by reference). Such potentiating effects of M.Ab.F11 on agonist-induced aggregation are depicted in FIG. 2. When subthreshold concentrations of ADP (0.5 mM) or M.Ab.F11 (0.3 mg/ml), respectively, were added separately to platelet suspensions, there was no aggregation (panel B). However, when subthreshold concentrations of ADP were added together with subthreshold concentrations of M.Ab.F11, a pronounced aggregation response was observed, reflecting the potentiating effect (see "M.Ab.F11 plus ADP" tracings in each panel). Similar potentiating effects were observed with thrombin (data not shown). As shown in Panels B and C of FIG. 2, the addition of 50 µM of F11R peptide 1 (SEQ ID NO: 1) or peptide 4 (SEQ ID NO: 4) completely inhibited the potentiation by M.Ab.F11 of ADP-induced platelet aggregation. In contrast to these two peptides, peptide 3 (SEQ ID NO: 3) (as shown in Panel D), did not inhibit the potentiation of ADP-induced platelet aggregation by subthreshold concentrations of M.Ab.F11. The lack of inhibition by F11R peptides 2 (SEQ ID NO: 2) and 5 (SEQ ID NO: 5) was the same as shown in FIG. 2D for peptide 3 (SEQ ID NO: 3).

Example 5

F11R-peptides inhibit the potentiation of collagen-induced platelet aggregation. The effect of F11R peptides on M.Ab.F11-induced potentiation of platelet aggregation induced by nonaggregating concentrations of collagen (0.5 µg/ml) also was examined. These results are shown in FIG. 4. Subthreshold concentrations of collagen and of M.Ab.F11 used here were determined separately for each blood donor. Panel A of FIG. 4 demonstrates that the selected concentrations of each of the agonists were not able to induce platelet aggregation when added alone. However, the addition of collagen just after adding M.Ab.F11 readily triggered a full-blown platelet aggregation. The potentiation by M.Ab.F11 of collagen-induced platelet aggregation could be completely blocked by F11R-peptide 1 (SEQ ID NO: 1), as shown in Panel B, as well as by peptide 4 (SEQ ID NO: 4), as shown in Panel C, but not with peptide 5 (SEQ ID NO: 5) (also shown in Panel C) nor with peptide 3 (SEQ ID NO: 3) (shown in panel D). The addition of sF11R (1 µg/ml) to platelet suspensions completely blocked the potentiation by M.Ab.F11 of both ADP- and collagen-induced platelet aggregation, and the results were the same as shown for peptides 1 (SEQ ID NO: 1) and 4 (SEQ ID NO: 4) in FIGS. 2 and 4.

Example 6

Figure 5:
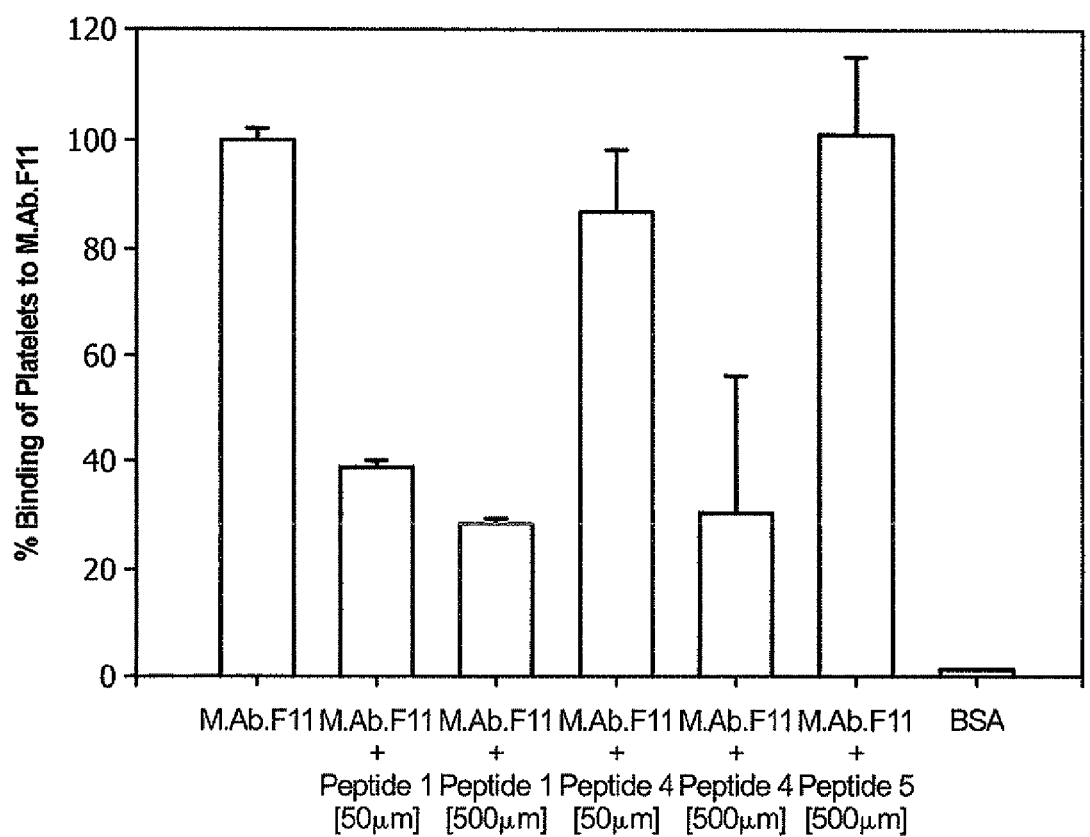
FIG. 5 shows inhibition of adhesion by F11R peptides (SEQ ID NOS: and 4).

Two specific F11R-peptides inhibit platelet adhesion to M.Ab.F11. The five peptides with sequences shown in Table 1 were tested also for their effects on the adhesion of platelets to immobilized M.Ab.F11 (150 ng/well). The left bar of FIG. 5 demonstrates the control adhesion measured without added peptide. Peptide 1 (SEQ ID NO: 1), added at 50 µM caused about 60% inhibition of the adhesion of platelets to immobilized M.Ab.F11, and with 500 µM of peptide 1 (SEQ ID NO: 1), about 70% inhibition was observed. Peptide 4 (SEQ ID NO: 4), at 50 µM, produced very little (10%) inhibition compared to peptide 1 (SEQ ID NO: 1) at similar concentrations. However, 500 µM of peptide 4 (SEQ ID NO: 4) produced approximately 70% inhibition in the adhesion of platelets to M.Ab.F11, similar to that observed with peptide 1 (SEQ ID NO: 1) at the same concentration. On the other hand, the addition of 500 µM (or higher) of peptides 2, 3 or 5 did not cause significant inhibition of platelet adhesion to M.Ab.F11.

Example 7

Three-dimensional structure of the recombinant human platelet F11R. A 3-dimensional structural model of the human platelet F11R, highlighting the two domains that are occupied by sequences of the platelet inhibitory peptides 1 and 4, are depicted in FIG. 1. From this modeling it appears that the N-terminal portion of the molecule (containing the sequence of peptide 1 (SEQ ID NO: 1)), forms a loop around the $1^{st}$ Ig-fold (containing the sequence of peptide 4 (SEQ ID NO: 4)) to form an "active pocket" containing the sequences of both peptides 1 and 4, arranged in an anti-parallel orientation. The data demonstrates that these two domains contain critical sites of the molecule that are responsible, at least in part, for triggering platelet aggregation, potentiation and adhesion by and to this immunologic agonist. This "active pocket" thus constitutes the stereospecific binding site for M.Ab.F11 (Kornecki et al. 1990, Supra), and for homophilic interactions of F11R molecules (Kornecki et al. (2001) *F11R: A Novel Receptor of the Immunoglobulin Superfamily Involved in the Adhesion and Aggregation of Human Platelets*, XV111th $15^{th}$ Congress, July, Paris, France 2001; Abs #54942, incorporated herein by reference).

The invention claimed is:

1. An isolated F11R-antagonist compound consisting of the amino acid sequence as set forth in SEQ ID NO: 1.

2. An isolated F11R-antagonist compound consisting of the amino acid sequence as set forth in SEQ ID NO: 4.

3. A pharmaceutical composition comprising the isolated F11R-antagonist according to claim 1.

4. A pharmaceutical composition comprising the isolated F11R-antagonist according to claim 2.

* * * * *